(12) United States Patent
Baker, Jr. et al.

(10) Patent No.: US 7,657,292 B2
(45) Date of Patent: Feb. 2, 2010

(54) METHOD FOR EVALUATING EXTRACELLULAR WATER CONCENTRATION IN TISSUE

(75) Inventors: Clark R. Baker, Jr., Castro Valley, CA (US); Joseph Schmitt, Andover, MA (US); Shannon Campbell, Oakland, CA (US); Nick Durr, Austin, TX (US); Carine Hoarau, Lafayette, CA (US); Rafeal Ostrowski, Pittsburg, CA (US); Martin Debreczeny, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 686 days.

(21) Appl. No.: 11/283,506

(22) Filed: Nov. 18, 2005

(65) Prior Publication Data

US 2007/0118027 A1    May 24, 2007

Related U.S. Application Data

(63) Continuation-in-part of application No. 10/699,610, filed on Oct. 30, 2003, now Pat. No. 7,239,902, which is a continuation-in-part of application No. 10/441,943, filed on May 20, 2003, now Pat. No. 7,236,811, which is a continuation of application No. 09/810,918, filed on Mar. 16, 2001, now Pat. No. 6,591,122.

(51) Int. Cl.
*A61B 5/145* (2006.01)
(52) U.S. Cl. ........................ 600/310; 600/476
(58) Field of Classification Search ............. 600/309, 600/310, 407, 473, 476
See application file for complete search history.

(56) References Cited

U.S. PATENT DOCUMENTS

| | | | |
|---|---|---|---|
| 3,998,550 | A | 12/1976 | Konishi et al. |
| 4,066,068 | A | 1/1978 | Nilsson et al. |
| 4,364,008 | A | 12/1982 | Jacques |
| 4,711,244 | A | 12/1987 | Kuzara |
| 4,723,554 | A | 2/1988 | Oman et al. |
| 4,805,623 | A | 2/1989 | Jobsis |
| 4,850,365 | A | 7/1989 | Rosenthal |
| 4,860,753 | A | 8/1989 | Amerena |

(Continued)

FOREIGN PATENT DOCUMENTS

CA        2353007 A1    6/2000

(Continued)

OTHER PUBLICATIONS

Wheeler, Owen H., "Near Infrared Spectra of Organic Compounds," Department of Chemistry, College of Agriculture and Mechanic Arts, University of Puerto Rico (Mar. 1929).

(Continued)

*Primary Examiner*—Eric F Winakur
*Assistant Examiner*—Etsub D Berhanu
(74) *Attorney, Agent, or Firm*—Fletcher Yoder

(57) ABSTRACT

The present disclosure provides systems, devices, and/or methods for assessing body fluid-related metrics and/or changes therein. The disclosure further provides systems, devices, and/or methods for correlating body fluid-related metrics in a particular tissue with the corresponding whole-body metric. The disclosure also provides, systems, devices, and/or methods for assessment of such metrics to facilitate diagnosis and/or therapeutic interventions related to maintaining and/or restoring body fluid balance.

30 Claims, 10 Drawing Sheets

U.S. PATENT DOCUMENTS

| | | | |
|---|---|---|---|
| 4,883,055 | A | 11/1989 | Merrick |
| 4,907,594 | A | 3/1990 | Muz |
| 5,057,695 | A | 10/1991 | Hirao et al. |
| 5,058,588 | A * | 10/1991 | Kaestle ................. 600/323 |
| 5,086,781 | A | 2/1992 | Bookspan |
| 5,111,817 | A | 5/1992 | Clark et al. |
| 5,146,091 | A | 9/1992 | Knudson |
| 5,224,478 | A | 7/1993 | Sakai et al. |
| 5,277,181 | A | 1/1994 | Mendelson et al. |
| 5,279,295 | A | 1/1994 | Martens et al. |
| 5,282,467 | A | 2/1994 | Piantadosi et al. |
| 5,337,745 | A | 8/1994 | Benaron |
| 5,337,937 | A | 8/1994 | Blank et al. |
| 5,348,004 | A | 9/1994 | Hollub |
| 5,355,880 | A | 10/1994 | Thomas et al. |
| 5,377,674 | A | 1/1995 | Kuestner |
| 5,499,627 | A | 3/1996 | Steuer et al. |
| 5,615,689 | A | 4/1997 | Kotler |
| 5,687,721 | A | 11/1997 | Kuhls |
| 5,701,902 | A | 12/1997 | Vari et al. |
| 5,720,284 | A | 2/1998 | Aoyagi et al. |
| 5,735,284 | A | 4/1998 | Tsoglin et al. |
| 5,747,789 | A | 5/1998 | Godik |
| 5,755,672 | A | 5/1998 | Arai et al. |
| 5,788,643 | A | 8/1998 | Feldman |
| 5,803,908 | A | 9/1998 | Steuer et al. |
| 5,827,181 | A | 10/1998 | Dias et al. |
| 5,833,602 | A | 11/1998 | Osemwota |
| 5,853,364 | A | 12/1998 | Baker, Jr. et al. |
| 5,860,919 | A | 1/1999 | Kiani-Azarbayjany et al. |
| 5,906,582 | A | 5/1999 | Kondo et al. |
| 6,064,898 | A | 5/2000 | Aldrich |
| 6,125,297 | A | 9/2000 | Siconolfi |
| 6,149,591 | A | 11/2000 | Henderson et al. |
| 6,178,342 | B1 | 1/2001 | Thompson et al. |
| 6,222,189 | B1 | 4/2001 | Misner et al. |
| 6,246,894 | B1 | 6/2001 | Steuer et al. |
| 6,280,396 | B1 | 8/2001 | Clark |
| 6,336,044 | B1 | 1/2002 | Ghiassi et al. |
| 6,370,426 | B1 | 4/2002 | Campbell et al. |
| 6,400,971 | B1 | 6/2002 | Finarov et al. |
| 6,402,690 | B1 | 6/2002 | Rhee et al. |
| 6,442,408 | B1 | 8/2002 | Wenzel et al. |
| 6,466,807 | B1 | 10/2002 | Dobson et al. |
| 6,488,677 | B1 | 12/2002 | Bowman et al. |
| 6,512,936 | B1 | 1/2003 | Monfre et al. |
| 6,591,122 | B2 | 7/2003 | Schmitt |
| 6,592,574 | B1 | 7/2003 | Shimmick et al. |
| 6,600,946 | B1 | 7/2003 | Rice |
| 6,606,509 | B2 | 8/2003 | Schmitt |
| 6,615,064 | B1 | 9/2003 | Aldrich |
| 6,635,491 | B1 | 10/2003 | Khalil et al. |
| 6,636,759 | B2 | 10/2003 | Robinson |
| 6,643,543 | B2 | 11/2003 | Takehara et al. |
| 6,654,620 | B2 | 11/2003 | Wu et al. |
| 6,668,181 | B2 | 12/2003 | Wenzel et al. |
| 6,675,029 | B2 | 1/2004 | Monfre et al. |
| 6,687,519 | B2 | 2/2004 | Steuer et al. |
| 6,777,240 | B2 | 8/2004 | Hazen et al. |
| 6,840,904 | B2 | 1/2005 | Goldberg |
| 6,849,046 | B1 | 2/2005 | Eyal-Bickels |
| 6,873,865 | B2 | 3/2005 | Steue et al. |
| 6,931,268 | B1 | 8/2005 | Kiani et al. |
| 6,950,699 | B1 | 9/2005 | Manwaring et al. |
| 6,954,661 | B2 | 10/2005 | Cho et al. |
| 6,961,598 | B2 | 11/2005 | Diab |
| 7,239,905 | B2 | 7/2007 | Kiani et al. |
| 7,257,433 | B2 | 8/2007 | Takamura et al. |
| 7,283,242 | B2 | 10/2007 | Thornton |
| 7,398,115 | B2 | 7/2008 | Lynn |
| 2001/0020122 | A1 | 9/2001 | Steuer et al. |
| 2003/0060693 | A1 * | 3/2003 | Monfre et al. ............ 600/322 |
| 2004/0127777 | A1 | 7/2004 | Ruchti et al. |
| 2004/0147034 | A1 | 7/2004 | Gore et al. |
| 2004/0230106 | A1 | 11/2004 | Schmitt et al. |
| 2004/0242976 | A1 * | 12/2004 | Abreu ..................... 600/315 |
| 2005/0065415 | A1 | 3/2005 | Cho et al. |
| 2005/0119538 | A1 | 6/2005 | Jeon et al. |
| 2005/0177046 | A1 | 8/2005 | Mills |
| 2005/0192493 | A1 | 9/2005 | Wuori |
| 2005/0256384 | A1 * | 11/2005 | Walker et al. ............ 600/316 |
| 2006/0020179 | A1 | 1/2006 | Anderson et al. |
| 2006/0020181 | A1 | 1/2006 | Schmitt |
| 2006/0052680 | A1 | 3/2006 | Diab |
| 2006/0084864 | A1 | 4/2006 | Schmitt et al. |
| 2006/0167350 | A1 | 7/2006 | Monfre et al. |
| 2006/0247506 | A1 | 11/2006 | Balberg et al. |

FOREIGN PATENT DOCUMENTS

| | | |
|---|---|---|
| DE | 19855521 A1 | 6/2000 |
| EP | 1135184 A1 | 6/2000 |
| EP | 1184663 A2 | 3/2002 |
| EP | 1491135 | 12/2004 |
| FR | 2710517 | 4/1995 |
| JP | 4-40940 | 2/1992 |
| JP | 5-329163 | 12/1993 |
| JP | 11-244266 | 9/1999 |
| JP | 2004 081427 A | 3/2004 |
| WO | WO 95/19562 A | 7/1995 |
| WO | WO 98/34097 | 8/1998 |
| WO | WO 00/32262 A1 | 6/2000 |
| WO | WO 2000/030530 A | 6/2000 |
| WO | WO 00/71025 A1 | 11/2000 |
| WO | WO 93/13706 A2 | 1/2001 |
| WO | WO 01/16577 A1 | 3/2001 |
| WO | WO 01/21068 A1 * | 3/2001 |
| WO | WO 2003/010510 A | 2/2003 |
| WO | WO 2005/041765 A | 5/2005 |

OTHER PUBLICATIONS

Pace, Nello, et al., "Studies on Body Composition: III. The body water and chemically combined nitrogen content in relation to fat content," Naval Medical Research Institute, Bethesda, Maryland (Jan. 11, 1945).

Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).

Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).

Forbes, R.M., et al., "The Composition of the Adult Human Body as Determined by Chemical Analysis," Division of Animal Nutrition, and the Department of Anatomy, University of Illinois, Jan. 19, 1953.

Buijs, K., et al., "Near-Infrared Studies of the Structure of Water. I. Pure Water," *The Journal of Chemical Physics*, vol. 39, No. 8, pp. 2035-2041 (Oct. 15, 1963).

Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).

Goldstein, R., et al., "The Near-Infrared Absorption of Liquid Water at Temperatures Between 27 and 209° C," *J. Quant. Spectrosc. Radiat. Transfer.*, vol. 4, pp. 441-451 (1964).

Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).

Houseman, R.A., et al., "The measurement of total body water in living pigs by deuterium oxide dilution and its relation to body composition," *Br. J. Nutr.*, vol. 30, pp. 149-156 (1973).

Krikorian, S. Edward, et al., "The identification and origin of N-H overtone and combination bands in the near-infrared spectra of simple primary and secondary amides," *Spectrochimica acta*, vol. 29A, pp. 1233-1246 (1973).

Lesser, G.T., et al., "Body water compartments with human aging using fat-free mass as the reference standard," *Am J. Physiol Regul Integr Comp Physiol.*, vol. 236, pp. 215-220 (1979).

Sheng, Hwai-Ping, et al., "A review of body composition studies with emphasis on total body water and fat," *The American Journal of Clinical Nutrition*, vol. 32., pp. 630-647 (Mar. 1979).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Fomon, Samuel J., et al., "Body composition of reference children from birth to age 10 years," The American Journal of clinical Nutrition, vol. 35, pp. 1169-1175, (May 1982).

Lanza, Elaine, "Determination of Moisture, Protein, Fat, and Calories in Raw Pork and Beef by near Infrared Spectroscopy," *Journal of Food Science*, vol. 48, pp. 471-474 (1983).

Martens, Harald, et al., "Understanding food research data," Food Research and Data Analysis, Applied Science Publishers, pp. 5-38 (1983).

Shields, R. G., Jr., et al., "Efficacy of Deuterium Oxide to Estimate Body Composition of Growing Swine"; *Journal of Animal Science*, vol. 57, No. 1, pp. 66-73, (1983).

Wolfgang, Arneth, "Multivariate Infrared and near-infrared Spectroscopy: rapid analysis of protein, fat and water in meat," *Food Res and Data Analysis, Proc from IUoST Symp, Oslo, Norway*, pp. 239-251 (1983).

Cohn, S.H., et al., "Assessment of cellular mass and lean body mass by noninvasive nuclear techniques," *J. Lab Clin Med.*, vol. 105, pp. 305-311 (1985).

Hannon, John P., et al., "Splenic red cell sequestration and blood volume measurements in conscious pigs," *Am J. Physiol.*, vol. 248, pp. R293-R301 (1985).

Potts, R.O., et al., "A Noninvasive, In Vivo Technique to Quantitatively measure Water Concentration of the Stratum Cornum Using Attenuated Total-Reflectance Infrared Spectroscopy," *Arch. Dermatol Res.*, vol. 277, pp. 489-495 (1985).

Cox, Patrick, et al., "Variations in Lipids in Different Layers of Porcine Epidermis," *J. Invest Dermatol.*, vol. 87, pp. 741-744 (1986).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Hedberg, Chrisopher L., et al., "The Time Course of Lipid Biosynthesis in Pig Epidermis," *J. Invest Dermatol.*, vol. 91, pp. 169-174 (1988).

Hedberg, Christopher L., et al., "The nonpolar Lipids of Pig Epidermis," *J. Invest Dermatol.*, vol. 90, pp. 225-229 (1988).

Trapp, Scott A., et al., "An improved spectrophotometric bromide assay for the estimation of extracellular water volume," *Clinica Chimica Acta.*, vol. 181, pp. 207-212, (1989).

Bommannan, D., et al., "Examination of Stratum Corneum Barrier Function In Vivo by Infrared Spectroscopy," *J. Invest Dermatol*, vol. 95, pp. 403-408 (1990).

Hannon, John P., et al., "Normal pHysiological Values for Conscious Pigs Used in Biomedical Research," *Laboratory Animal Science*, vol. 40, No. 3, May 1990.

Mak, Vivien H.W., et al., "Oleic Acid Concentration and Effect in Human Stratum Corneum: Non-Invasive determination By Attenuated Total Reflectance Infrared Spectroscopy In Vivo," *Journal of Controlled Release*, vol. 12, pp. 67-75 (1990).

Edwardson, P. et al., "The Use of FT-IR for the Determination of Stratum Corneum Hydration in Vitro and in Vivo," J. *of Pharmaceutical & Biomed. Analysis*, vol. 9, Nos. 10-12, pp. 1089-1094, 1991.

Drummer, C., et al., "Effects of an acute saline infusion on fluid and electrolyte metabolism in humans," *Am J. Physiol.*, vol. 262, pp. F744-F754 (1992).

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Diaz-Carrillo, E., et al., "Near infrared calibrations for goat's milk components; protein, total casein, $\alpha_s$ -, $\beta$- and $\kappa$-caseins, fat and lactose," *J. near Infrared Spectrosc.*, vol. 1, pp. 141-146 (1993).

Martin, K., "Direct Measurement of Moisture in Skin by NIR spectroscopy," *J. Soc. Cosmet. Chem.*, 44:249-261 (1993).

Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).

Thompson et al., "Can bioelectrical impedance be used to measure total body water in dialysis patients?", *Physiol Meas.*, 14:455-461 (1993).

Bewig, Karen M., et al., "Discriminant Analysis of Vegetable Oils by Near-Infrared Reflectance Spectroscopy," *JAOCS*, vol. 71, No. 2, pp. 195-200 (Feb. 1994).

Kamishikiryo-Yamashita, Hiromi, et al, "Protein Content in Milk by Near-Infrared Spectroscopy," *Journal of Food Science*, vol. 59, No. 2, pp. 313-315 (1994).

Matcher, S. J., et al., "Absolute quantification of deoxyhaemoglobin concentration in tissue near infrared spectroscopy," *Phys. Med. Biol.*, vol. 39, pp. 1295-1312 (1994).

Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C., et al., "Protein composition of cornified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-72.

Warren, Joan L., et al., "The burden and Outcomes Associates with Dehydration among US Elderly, 1991," *American Journal of Public Health*, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," *Anesth Analg.*, vol. 80, pp. 135-142, (1995).

Kisch, Hille, et al., "Accuracy and reproducibility of the measurement of actively circulating blood vol. with an integrated fiberoptic monitoring system," *Critical Care Medicine*, vol. 23, No. 5, pp. 885-893 (1995).

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Quiniou, N., et al., "Prediction of Tissular Body Composition from Protein and Lipid Deposition in Growing Pigs," *J. Anim. Sci.*, vol. 73, pp. 1567-1575, (1995).

Avis, N.J., et al.; "In vitro multifrequency electrical impedance measurements and modeling of the cervix in late pregnancy", *Physiological Measurement*, vol. 17, pp. A97-A103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet, vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr*. 64(suppl):489S-97S (1996).

Kumar, Gitesh, et al., "Non-Invasive Optical Assessment of Tissue Hydration," *International conference on Biomedical Engineering*, Jun. 3-5 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.* vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in female athletes," Journal of Applied Physiology, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging versus Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water," *Critical Care*, vol. 3, pp. R19-R24 (1999).

Marken Lichtenbelt, Wouter D. Van, et al., "Increased extracellular water compartment, relative intracellular water compartment, after weight reduction," *Journal of Applied Physiology*, vol. 87, pp. 294-298 (1999).

Rennie, Michael J., "Perspectives—Teasing out the truth about collagen," *Journal of Physiology* vol. 521, p. 1 (1999).

Sowa et al., "New-infrared spectroscopic assessment of tissue hydration following surgery", *Journal of Surgical Research*, 86:62-69 (1999).

Wagner, J.R., et al., "Analysis of Body Composition Changes of Swine During Growth and Development," *J. Anim. Sci.*, vol. 77, pp. 1442-1466 (1999).

Wang, Zimian, et al., "Hydration of fat-free body mass: new physiological modeling approach," *Am. J. Physiol.*, vol. 276, pp. E995-E1003 (1999).

Wang, Zimian, et al., "Hydration of fat-free body mass: review and critique of a classic body-composition constant," *Am J. Clin. Nutr.*, vol. 69, pp. 833-841 (1999).

Ward, L., et al., "Multiple frequency bioelectrical impedance analysis: a cross-validation study of the inductor circuit and Cole models," *Physiol. Meas.*, vol. 20, pp. 333-347 (1999).

Well, Jonathan CK, et al., "Four-component model of body composition in children: density and hydration of fat-free mass and comparison with simpler models," *Am J. Clin. Nutr.*, vol. 69, pp. 904-912 (1999).

Butte, Nancy F., et al., "Body Composition during the First 2 Years of Life; An Updated Reference," *Pediatric Research*, vol. 47, No. 5, pp. 578-585 (2000).

Feigenbaum, Matthew S., et al., "Contracted Plasma and Blood Volume in Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).

Lucassen, G., et al., "Water Content and Water Profiles in Skin Measured by FTIR and Raman Spectroscopy," *Proc. SPIE*, vol. 4162, pp. 39-45 (2000).

Plank, L. D., et al., "Similarity of Changes in Body Composition in Intensive Care Patients following Severe Sepsis or Major Blunt Injury," *Annals New York Academy of Sciences*, pp. 592-602 (2000).

Ritz, P., et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R., et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael, et al., "Visualization of cutaneous hemoglobin oxygenation and skin hydration using near-infrared spectroscopic imaging," *Skin Research and Technology*, vol. 7, pp. 238-245, (2001).

Bray, George A., et al., "Evaluation of body fat in fatter and leaner 10-y-old African American and white children: the Baton Rouge Children's Study," *Am J. Clin Nutr*, vol. 73, pp. 687-702 (2001).

Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M380 (2001).

Divert, Victor E., "Body Thermal State Influence on Local Skin Thermosensitivity," *International Journal of Circumpolar Health*, vol. 60, pp. 305-311(2001).

Du, Y., et al., "Optical properties of porcine skin dermis between 900 nm and 1500 nm," *Phys. Med. Biol.*, vol. 46, pp. 167-181 (2001).

Endo, Yutaka, et al., "Water drinking causes a biphasic change in blood composition in humans," *Pflügers Arch— Eur J. Physiol*, vol. 442, pp. 362-368 (2001).

Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).

Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Kamba, Masayuki, et al., "Proton magnetic resonance spectroscopy for assessment of human body composition," *Am J. Clin. Nutr.*, vol. 73, pp. 172-176 (2001).

Lever, M., et al., "Some ways of looking at compensatory kosmotropes and different water environments," *Comparative Biochemistry and Physiolog.*, vol. 130, Part A, pp. 471-486, (2001).

Mingrone, G., et al., "Unreliable use of standard muscle hydration value in obesity," *Am J. Physiol Endocrinal Metab.*, vol. 280, pp. E365-371, (2001).

Ritz, Patrick, "Chronic Cellular Dehydration in the Aged Patient," Journal of Gerontology, vol. 56A, No. 6, pp. M349-M352 (2001).

Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).

Schnickel, A.P., et al., "Evaluation of alternative measures of pork carcass composition," *J. Anim. Sci.*, vol. 79, pp. 1093-1119, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Tsukahara, K., et al., "Dermal fluid translocation is an important determinant of the diurnal variation in human skin thickness," *British Journal of Dermatology*, vol. 145, pp. 590-596 (2001).

Vescovi, Jason D., et al., "Evaluation of the BOD POD for estimating percentage body fat in a heterogeneous group of adult humans," *Eur J. Appl. Physiol.*, vol. 85, pp. 326-332 (2001).

Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).

Watson, Walter, "Hydration of fat-free body mass: new physiological modeling approach," *Am J. Physiol. Endocrinol. Metab.*, Letters to the Editor, vol. 278, pp. E752-E753 (2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Blank, T.B., et al., "Clinical Results from a Non-Invasive Blood Glucose Monitor," *Photonics West 2002 Meeting*, San Jose, California, Jan. 19-25, 2002 (25 pages).

Chamney, Paul W., et al., "A new technique for establishing dry weight in hemodialysis patients via whole body bioimpedance," *Kidney International*, vol. 61, pp. 2250-2258 (2002).

Drobin, Dan, et al., "Kinetics of Isotonic and Hypertonic Plasma Volume Expanders," *Anesthesiology*, vol. 96, No. 6, pp. 1371-1380 (Jun. 2002).

Endo, Yutaka, et al., "Changes in Blood Pressure and Muscle Sympathetic Nerve Activity during Water Drinking in Humans," *Japanese Journal of Physiology*, vol. 52, pp. 421-427 (2002).

Haga, Henning A., et al., "Motor responses to stimulation during isoflurane anaesthesia in pigs," *Veterinary Anaesthesia and Analgesia*, vol. 29, pp. 69-75 (2002).

Klaus, Stephan, et al., "Assessment of fluid balance by measurement of skin tissue thickness during clinical anaesthesia, " *Clin. Physiol & Func. Im.*, vol. 22, pp. 197-201 (2002).

Meglinski, Igor V., et al., "Quantitative assessment of skin layers absorption and skin reflectance spectra simulation in the visible and near-infrared spectral regions," *Physiol Meas.*, vol. 23, pp. 741-753, (2002).

Perez-de-Sá, Valéria, et al., "Mild Hypothermia Has Minimal Effects on the Tolerance to Severe Progressive Normovolemic Anemia in Swine," *Anesthesiology*, Vo. 97, pp. 1189-1197 (2002).

Ponec, Maria, et al., "Charactrization of Reconstructed Skin Models," *Skin Pharmacol Appl Skin Physiol.*, vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Bommel, Jasper, et al., "Intestinal and Cerebral Oxygenation during Severe lsovolemic Hemodilution and Subsequent Hyperoxic Ventilation in a Pig Model," *Anesthesiology*, vol. 97, No. 3, pp. 660-670 (Sep. 2002).

Wong, William W., et al., "Evaluating body fat in girls and female adolescents: advantages and disadvantages of dual-energy X-ray absorptiometry," *Am J. Clin Nutr.*, vol. 76, pp. 384-389 (2002).

Baković, Darija, et al., "Spleen volume and blood flow response to repeated breath-hold apneas," *J. Appl. Physiol.*, vol. 95, pp. 1460-1466 (2003).

Bartok, Cynthia, et al., "Measurement of nutritional statusin simulated microgravity by bioelectrical impedance spectroscopy," *J. Appl. Physiol.*, vol. 95, pp. 225-232 (2003).

Bouwstra, Joke A., et al., "Water Distribution and Related Morphology in Human Stratum Corneum at Different Hydration Levels," *J. Invest Dermatol*, vol. 150, pp. 750-758 (2003).

Butte, Nancy F., et al., "Composition of gestational weight gain impacts maternal fat retention and infant birth weight," *Am J. Obstet Gynecol*, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," *The Journal of TRAUMA, Injury, Infection, and Critical Care*, vol. 54, No. 5, pp. S20-S25 (May Supplement 2003).

Cook, Lynda S., "IV Vluid Resuscitation," *Journal of Infusion Nursing*, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).

Grandjean et al., "Hydration: issues for the $21^{st\ century}$," *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Kemming, G.I., et al., "Hyperoxic ventilation at the critical haematocrit," *Resuscitation*, vol. 56, pp. 289-297 (2003).

Kurita, T., et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses to isotonic saline infusion after 3 days' dead-down tilt vs. supine and seated positions," *Acta Physiol Scand.*, vol. 177, pp. 167-176, (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol., 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, ppl 185-190 (Apr. 2003).

Mentes, Janet C., et al., "Reducing Hydration=-Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

Petäjäl., et al., "Dielectric constant of skin and subcutaneous fat to assess fluid changes after cardiac surgery", *Physiological Measurement*, 24: 3383-390, 2003.

Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Robinson, Martin P., et al., "A novel method of studying total body water content using a resonant cavity: experiments and numerical simulation," *Phys. Med. Biol.*, vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinal. Metab*, vol. 284, pp. E267-E273 (2003).

Windberger, U, et al., "Whole blood viscosity, plasma viscosity and erythrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Ackland, G.L., et al., "Assessment of preoperative fluid depletion using bioimpedance analysis," *British Journal of Anaesthesia*, vol. 92, No. 1, pp. 134-136 (2004).

Arimoto et al., "Non-contact skin moisture measurement based on near-infrared spectroscopy", *Applied Spectroscopy*, 58(12):1439-1445 (2004).

Davidhizr, R., et al., "A review of the literature on how important water is to the world's elderly population," *International Nursing Review*, vol. 51, pp. 159-166 (2004).

Dullenkopf, A., et al., "Non-invasive monitoring of haemoglobin concentration in paediatric surgical patients using near-infrared spectroscopy," *Anaesthesia*, vol. 59, pp. 453-458 (2004).

Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M., et al., "Influence of hydration and experimental length scale on the mechanical response o human skin in vivo, using optical coherence tomography," *Skin Research and Technology*, vol. 10, pp. 231-241 (2004).

Hieda, I., et al., "Basic characteristics of the radio imaging method for biomedical application," *Medical Engineering & Physics*, vol. 26, pp. 431-437 (2004).

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on In Vitro Model Human Skin," *Lasers in Surgery and Medicine*, vol. 34, pp. 146-154 (2004).

Kyle, Urusula G., et al., "Bioelectrical impedance anslysis—part II: utilization in clinical practice," *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 113-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a enw dielectric device to assess changes of tissue water in skin and subcutaneous fat," *Physiol Meas.*, vol. 25, pp. 447-454, (2004).

Rhodes, Andrew, et al., "Book Report—Haemodynamic monitoring in critically ill patients," *Critical Care*, vol. 8, p. 203 (2004).

St-Onge, Marie-Pierre, et al., "Dual-energy X-ray absorptiometry lean soft tissue hydration: independent contributions of intra-and extracellular water," *Am J. Physiol. Endrocrinol Metab*, vol. 287, pp. E842-E847, Jul. 6, 2004.

Schou, A. J., et al., "Methodological aspects of high-frequency ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol Endocrinol. Metab.*, vol. 286, pp. E123-E128 (2004).

Arimoto, Hidenobu, et al., "Depth profile of diffuse reflectance near-infrared spectroscopy for measurement of water content in skin," *Skin Research and Technology*, vol. 11, pp. 27-35 (2005).

Burmeister, J.J., et al., "Spectroscopic considerations for noninvasive blood glucose measurements with near infrared spectroscopy", *LEOS Newsletter*, vol. 12, No. 2, 1998, http://www.ieee.org/organizations/pubs/newsletters/leos/apr98/infrared.htm (last accessed, Nov. 30, 2005).

Haroun, D., et al., "Composition of the fat-free mass in obese and nonobese children: matched case—control analyses," *International Journal of Obesity*, vol. 29, pp. 29-36 (2005).

Ivorra, Antoni, et al., "Bioimpedance dispersion width as a parameter to monitor living tissues," *Physiol. Meas.*, vol. 26, pp. S165-S173 (2005).

Remote ICU Monitoring, *U.S. News & World Report*, pp. 45-61 (Aug. 1, 2005).

Sarkar, Shubho R., et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K., et al., "Noninvasive blood glucose analysis using near infrared absorption spectroscopy", MIT Home Automation and Healthcare Consortium, Progress Report No. 2-5, http://darbelofflab.mit.edu/ProcressReports/HomeAutomation/Report2-5/Chapter04.pdf (last accessed, Nov. 30, 2005).

García-Olmo, J., et al., "Advantages and disadvantages of multiple linear regression and partial least squares regression equations for the prediction of fatty acids," pp. 253-258 (undated).

Wang, Zimian, et al., "Cellular-Level Body Composition Model—A New Approach to Studying Fat-free Mass Hydration," *Annals New York Academy of Sciencei*, pp. 306-311 (undated).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

\* cited by examiner

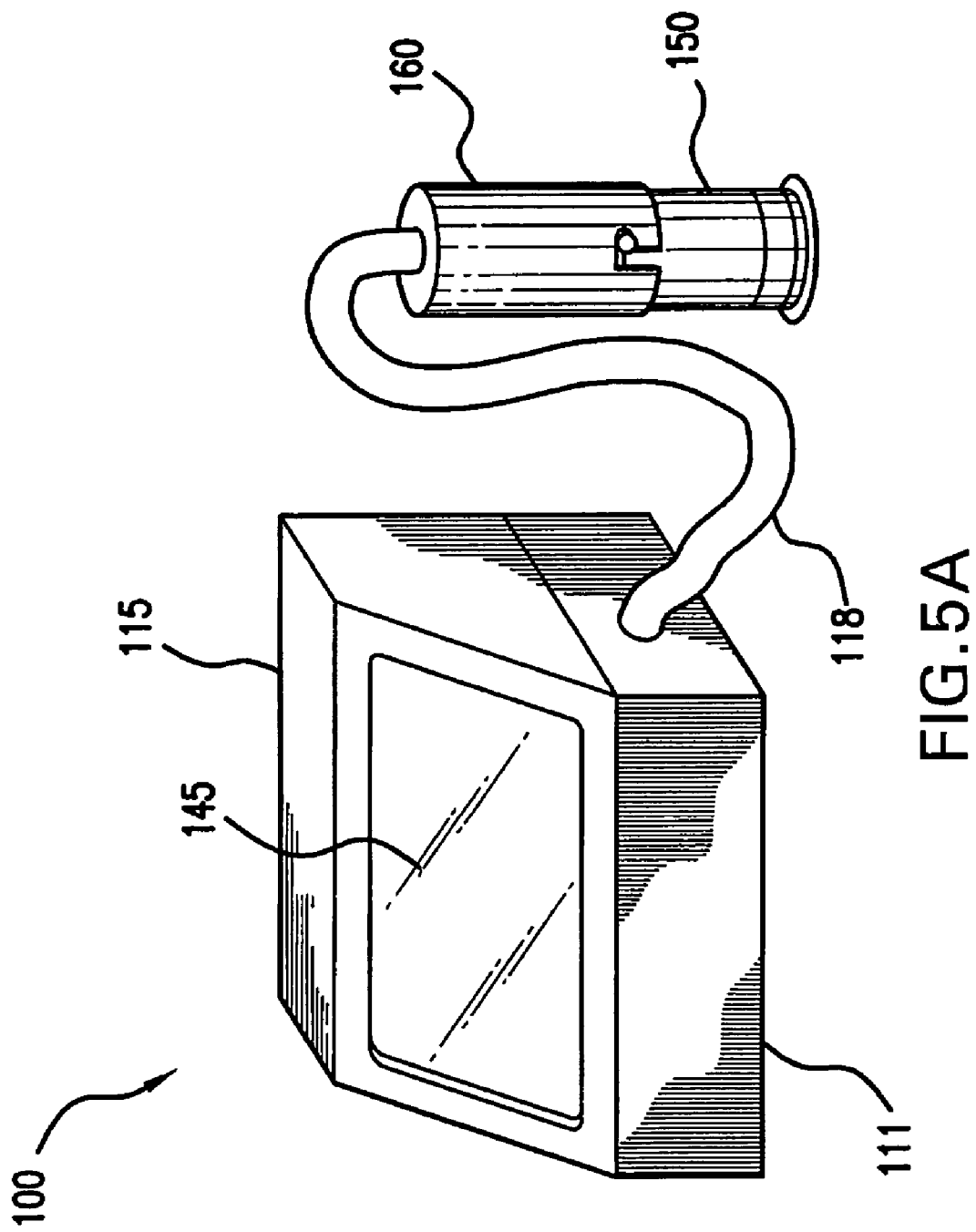

METHOD FOR EVALUATING EXTRACELLULAR WATER CONCENTRATION IN TISSUE

CROSS-REFERENCE TO RELATED APPLICATIONS

The present application is a continuation-in-part of U.S. patent application Ser. No. 10/699,610, filed on Oct. 30, 2003, now U.S. Pat. No. 7,239,902 which is a continuation-in-part of U.S. patent application Ser. No. 10/441,943, filed on May 20, 2003 now U.S. Pat. No. 7,236,811, which is a continuation of U.S. patent application Ser. No. 09/810,918, filed on Mar. 16, 2001, now U.S. Pat. No. 6,591,122, and are incorporated herein by reference.

TECHNICAL FIELD

The present disclosure is related to devices and methods for assessing and evaluating one or more body-fluid metrics.

BACKGROUND

Dehydration may be associated with increased risk of developing dental disease, urinary tract infections, bronchopulmonary disorders, kidney stones, constipation, poor immune function, cardiovascular pathologies, and impaired cognitive function. The maintenance of body fluid balance may often be one of the foremost concerns in the care and treatment of critically ill patients, yet physicians have access to few diagnostic tools to assist them in this vital task. Patients with congestive heart failure, for example, frequently suffer from chronic systemic edema, which must be controlled within tight limits to ensure adequate tissue perfusion and prevent dangerous electrolyte disturbances. Dehydration of infants and children suffering from diarrhea can be life-threatening if not recognized and treated promptly.

The most common method for judging the severity of edema or dehydration is based on the interpretation of subjective clinical signs (e.g., swelling of limbs, dry mucous membranes), with additional information provided by measurements of the frequency of urination, heart rate, urea nitrogen (BUN)/creatinine ratios, and blood electrolyte levels and/or protein levels. None of these existing single-variable assessments, however, provide a means to easily determine water retention or loss.

SUMMARY

Therefore, there exists a need for methods and devices for monitoring body fluid (e.g., water) metrics that are less invasive, less subjective, and more accurate. The present disclosure, according to some specific example embodiments, relates to systems, devices, and/or methods for assessing body fluid-related metrics and changes therein. Other specific example embodiments, according to the present disclosure, further relate to systems, devices, and/or methods for correlating body fluid-related metrics, e.g., in a particular tissue with the corresponding whole-body metric.

The disclosure provides, according to some specific example embodiments, methods for assessing an extracellular fluid metric in a subject, including (a) emitting light of at least one wavelength from a source toward a tissue site of interest, wherein a portion of the emitted light is reflected by the tissue site of interest, (b) detecting at least one wavelength of the light reflected by the tissue site of interest from a position about zero millimeters to about twenty millimeters (e.g., from about one millimeter to about five millimeters) from the source, (c) emitting light of at least one wavelength from a source toward a reference tissue site, wherein a portion of the emitted light is reflected by the reference tissue site, (d) detecting at least one wavelength of the light reflected by the reference tissue site from a position about zero millimeters to about twenty millimeters (e.g., from about one millimeter to about five millimeters) from the source, and (e) processing detected reflected light from the tissue site of interest and detected reflected light from the reference tissue site to compute the extracellular water metric. According to some specific example embodiments, the disclosure further provides methods for assessing an extracellular water metric in a subject including (a) assessing a first localized water metric at a first tissue site in the subject, (b) assessing a second localized water metric at a second tissue site in the subject, and (c) processing the first and second localized water metrics to produce a whole-body extracellular water metric. In other specific example embodiments, the disclosure provides methods for assessing changes in extracellular fluid volume including (a) measuring a first optical signal received by an optical detector at a tissue site having a first hydrostatic pressure, (b) measuring a second optical signal received by an optical detector at a tissue site having a second hydrostatic pressure, (c) estimating fluid content from the first and second sets of optical signals, and (d) determining the relationship of said fluid-content estimates to the differences in hydrostatic pressure and estimating changes in extracellular fluid volume from said relationship. The disclosure additionally provides systems and/or devices for assessing a whole body fluid metric in a subject including a local fluid content probe configured to assess a local fluid metric at a tissue site of interest, a local fluid content probe configured to assess a local fluid metric at a tissue reference site, and a processing device, wherein the processing device may be operably coupled to the local fluid content probe configured to assess a local fluid metric at a tissue site of interest, operably coupled to the local fluid content probe configured to assess a local fluid metric at a tissue reference site, and configured to process a local fluid content metric at a tissue site of interest and a local fluid content metric at a tissue reference site to produce a whole-body fluid content metric. In other specific example embodiments, systems and/or devices for assessing a body fluid metric in a subject may include a local fluid content probe configured to assess a local fluid content metric at a tissue site, a location information sensor configured to assess location information of the probe, the tissue site of interest, or the probe and the tissue site of interest, and a processor, wherein the processor may be operably coupled to the local fluid content probe, operably coupled to the location information processor, and configured to process a local fluid content metric and location information to produce an extracellular fluid metric.

In some specific example embodiments of the disclosure, systems and/or devices for assessing an extracellular fluid content metric may include a means for assessing a fluid content metric at a tissue site at a first hydrostatic pressure, a means for assessing a fluid content metric at a tissue site at a second hydrostatic pressure, and a means for processing the fluid content metric at the tissue site at the first hydrostatic pressure and the fluid content metric at the tissue site at the second hydrostatic pressure to produce an extracellular fluid content metric.

According to some specific example embodiments of the disclosure, probes for assessing a body fluid metric may include a probe housing configured to be placed proximal to a tissue site of interest, a near infrared light emission fiber optic cable connected to the probe housing and configured to conduct radiation of at least one wavelength to the tissue location, a near infrared light detection fiber optic cable connected to the probe housing and configured to receive at least one wavelength of radiation from the tissue location, and a tissue compressor configured to alter (e.g., increase or decrease) the hydrostatic pressure of a tissue site (e.g., a tissue site of interest, a tissue reference site, or both a tissue site of interest and a tissue reference site). In some specific example embodiments, a probe may further include at least one sterile surface (e.g., where the probe may be associated with and/or in contact with damaged tissue or other tissue that is sensitive to contamination).

BRIEF DESCRIPTION OF THE DRAWINGS

Some specific example embodiments of the disclosure may be understood by referring, in part, to the following description and the accompanying drawings, wherein:

FIG. 5A shows an isometric view of one example of a system with a disposable water probe in an engaged position according to the teachings of the present disclosure;

DETAILED DESCRIPTION

Figure 1:
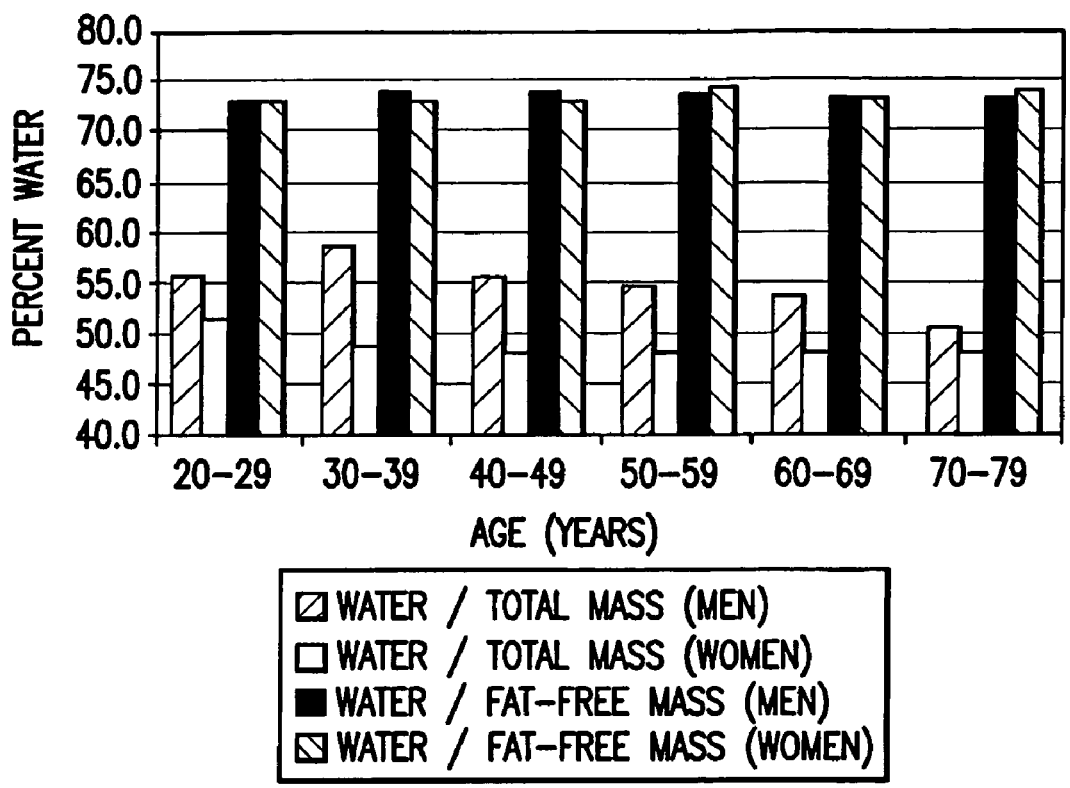
FIG. 1 is a bar graph of water content as a percentage of total mass and lean mass for men and women between the ages of 20 and 79.

According to some specific example embodiments, systems, devices, and/or methods of the disclosure may be useful in assessing, monitoring, and/or adjusting fluid, e.g., water, status in a subject or in any portion of a subject. For example, various fluids, as well as diuretics, are commonly administered multiple times to patients in surgery or intensive care without assessing patient hydration. In the absence of such feedback, the patient may be exposed to a risk of inadequate or excessive systemic hydration. According to another specific example embodiment, the systems, devices, and/or methods of the disclosure may contribute to minimizing this risk through assessment of one or more body-fluid related metrics. According to a further specific example embodiment, the systems, devices, and/or methods of the disclosure may be applied to any tissue and/or region of the subject's body. Body-fluid metrics may be assessed in any multicellular organism and/or any portion of a multicellular organism. In some specific example embodiments, the subjects may be mammals (or other animals). In other specific example embodiments, mammalian subjects may be human.

Water may generally partition into one of two compartments in the body, namely, inside cells (the intracellular compartment) and outside of the cells (the extracellular compartment). The extracellular compartment is further divided into vascular and interstitial compartments. According to a yet further specific example embodiment, systems, devices, and/or methods of the disclosure may allow assessment of body-fluid related metrics including, without limitation, (a) total water fraction ($f_w^T$), (b) fat-free and/or lean tissue water fraction ($f_w^L$), (c) intravascular water fraction ($f_w^{IV}$), (d) extravascular water fraction ($f_w^{EV}$), (e) interstitial water fraction ($f_w^{IS}$), (f) intracellular water fraction ($f_w^{IC}$), (g) extracellular water fraction ($F_W^{EC}$), and/or (h) combinations thereof.

Several methods of quantitating fluid, e.g., water, in the body may be used in accordance with the teachings of the present disclosure including, without limitation, bioimpedance, transepidermal water loss, viscoelastic measurements, dielectric conductance, optical spectrophotometry, magnetic resonance, ultrasound, and/or combinations thereof. For example, bioimpedance analysis and/or bioelectrical impedance spectroscopy may be used to apply an electrical current to assess tissue conductivity and, thereby, obtain a local and/or systemic fluid metric.

Any tissue site of the subject's body may be assessed using the systems, devices, and/or methods of the disclosure. In some specific example embodiments, the fluid, e.g., water, content of a site at or near the surface of the skin may be assessed. In other specific example embodiments, the water content of localized tissue sites at the surface of or within an organ may be assessed. Organs that may be assessed include, without limitation, the brain, the eyes, the nose, the mouth, the esophagus, the stomach, the skin, the intestines, the liver, the gall bladder, the pancreas, the spleen, the heart, blood, the lungs, the kidneys, the liver, the vagina, the cervix, the uterus, the fallopian tubes, the ovaries, the penis, the testes, the prostate, the bladder, and/or the pancreas. Tissues that may be assessed include, without limitation, muscles, bones, adipose, tendons, and/or ligaments.

Fluid Assessment

According to some non-limiting specific example embodiments of the disclosure, a body-fluid metric may be assessed in a single tissue. Such single-site assessments may be combined with additional information to evaluate a subject's whole-body water status in terms of the same metric and/or another metric. For example, an assessment site may be chosen based on an empirical determination that its water status is closely correlated with a whole-body fluid metric. Such sites may include, without limitation, the midline of the torso of a subject lying on his or her side and the forehead of a subject whose heart is positioned below the forehead and the whole-body metric may be fat-free percent water. Other sites may also be utilized.

The disclosure also provides specific example embodiments in which a whole-body metric may be used as a proxy for a tissue-specific body-fluid metric based on a demonstrated, calculated, or estimated direct or proportional correlation. In one example, a whole-body fluid metric may be obtained and/or used to estimate and/or determine the corresponding local body fluid metric. A whole-body fluid metric, such as total interstitial volume, may also be used as a proxy for a different local metric, such as, e.g., local interstitial volume.

The method of diffuse reflectance or transmittance near-infrared ("NIR") spectroscopy may be employed to measure the fraction of fluid, e.g., water, in a tissue. An increase or decrease in the fluid, e.g., water, content of the skin produces unique alterations of its NIR reflectance spectrum in three primary bands of wavelengths (950-1400 nm, 1500-1800 nm, and 2000-2300 nm) in which non-heme proteins (primarily keratin, collagen, and elastin), lipids, hemoglobin, and water absorb.

The tissue water fraction, $f_w$, may be defined as the ratio of the concentration of water and the sum of the absorbances of water and other constituents of the tissue, or:

$$f_w = \frac{C_w}{C_T} \quad (1)$$

where $C_w$ is the concentration of water and $C_T$ is the concentration of a combination of tissue constituents. Concentration may be expressed, in some embodiments, in units of fractional weight, fractional volume, molarity, molarity or other units. As demonstrated by numerical simulations and experimental studies, the tissue water fraction may be measured in the presence of nonspecific scattering variation, temperature, and other interfering variables.

The concentrations of tissue constituents are computed by combining tissue reflectance (or transmittance) measured at different spectral wavelength The absorbance of various constituents of tissue, other than water, may be included in these measurements. For example, in one specific example embodiment, all of the other major tissue constituents, such as non-heme protein, lipid ("fat"), and hemoglobin, may be included, resulting in the computation of the total tissue water fraction, $f_w^T$.

In other specific example embodiments, certain constituents of the tissue may be specifically excluded from the measured tissue water fraction. The disclosure contemplates the use of any means of excluding a tissue constituent including, without limitation, spectroscopic methods, physical methods, and/or computational methods.

Non-limiting examples of spectroscopic methods for the exclusion of certain tissue constituents from the computation of tissue water fraction are disclosed herein. In one type of specific example embodiment, spectral regions may be chosen where the absorbance contribution due to a selected tissue constituent may be small. For example, reflectance or transmittance may be measured at wavelengths greater than approximately 1150 nm to reduce the influence of hemoglobin absorption. In another, the absorbance contribution due to a tissue constituent may be cancelled by appropriately combining spectroscopic measurements made at multiple wavelengths. In the case of hemoglobin, reflectance or transmittance may be measured at wavelengths as short as 950 nm, but the influence of hemoglobin absorbance may be reduced by appropriately combining measurements of reflectance or transmittance at multiple wavelengths.

In some specific example embodiments, such spectroscopic methods may be used to exclude the absorbance due to lipid from $C_T$. Doing so yields the fractional water in fat-free or lean tissue, $f_w^L$.

Non-limiting examples of physical methods for excluding certain tissue constituents include (a) exerting a force on the assessment site and (b) placing the source-detector in a defined position relative to the assessment site. The force applied to the assessment site may be a gravitational force. For example, an assessment site that is below the center of mass (e.g., an ankle) may contain mobile constituents. To reduce or eliminate mobile constituents from measurement, the subject may be, e.g., reoriented so that the assessment site is above the subject's center of mass (e.g., having the subject lie on a hospital bed and elevating the ankle above the heart). Without being limited to any mechanism of action, mobile tissue constituents may, in response to gravity, flow out of the assessment site when it is above the center of mass.

Force applied to the assessment site may also be pressure. In some specific example embodiments, fractional water may be measured before and after the application and/or release of pressure at the assessment site, allowing the mobile intravascular or interstitial portion of the tissue to be included or excluded from the measurement. Pressure may be applied to the assessment site by any means including, without limitation, using a compression weight, cuff, belt or other device. By appropriate application of pressure to the assessment site, it may be possible to assess the fractional water content in the intravascular space, $f_w^{IV}$, and/or the extravascular space, $f_w^{EV}$ or the interstitital space or intracellular space In additional specific example embodiments, these measurements may be accomplished by photoplethysmography, e.g., by taking advantage of the natural arterial pulsation of blood through tissue.

Exclusion of the absorbance of some tissue constituents from the assessment may also be accomplished by selective placement of the source-detector relative to the assessment site. In some specific example embodiments, a source and a detector may be separated from each other by, about zero millimeters to about twenty millimeters (e.g., from about one millimeter to about five millimeters, or as much as 6.5 milimeters). However, depending on the site and the source-detector, other separation distances may be utilized. Separation may target the dermis while avoiding shallow penetration that would be indicative only of the stratum corneum layer of the skin. Separation may also avoid deep penetration into the underlying, high fat-content layer, or even further into bone-containing layers. To avoid shunting light through the superficial layers of the epidermis, the light source and/or detector may be configured to have low numerical apertures, e.g., less than about 0.3 radians. However, depending on the light source and/or detector, other apertures may be used.

Sensitivity of water fraction assessments to scattering variations may be minimized, if necessary, by, e.g., closely matching the optical path lengths through the dermis at the wavelengths at which the reflectances are measured. This matching may be achieved by judicious selection of wavelengths, e.g., wavelength sets, that have similar absorption scattering characteristics. Such wavelengths and/or wavelength sets may be selected from any one of the three primary wavelength bands (950-1400 nm, 1500-1800 nm, and 2000-2300 nm) discussed above. Wavelengths, wavelength pairs, and/or sets may, according to some specific example embodiments, be chosen from within one of these three primary bands, rather than from across these bands. For example, the wavelength pair of 1180 and 1300 nm is a wavelength set wherein the lengths of the optical paths through the dermis at these wavelengths are matched as closely as possible. Within a band, wavelengths may be chosen, according to some specific example embodiments, that differ by from about one (1) nanometer up to about four hundred fifty (450) nanometers. For example, wavelengths within a band may be chosen that differ by about 5 nanometers, about 10 nanometers, about 15 nanometers, about 20 nanometers, about 25 nanometers, about 30 nanometers, about 35 nanometers, about 40 nanometers, about 45 nanometers, about 50 nanometers, about 55 nanometers, about 60 nanometers, about 65 nanometers, about 70 nanometers, about 75 nanometers, about 80 nanometers, about 85 nanometers, about 90 nanometers, about 95 nanometers, about 100 nanometers, about 105 nanometers, about 110 nanometers, about 115 nanometers, about 120 nanometers, about 125 nanometers, about 130 nanometers, about 135 nanometers, about 140 nanometers, about 145 nanometers, about 150 nanometers, about 155 nanometers, about 160 nanometers, about 165 nanometers, about 170 nanometers, about 175 nanometers, about 180 nanometers, about 185 nanometers, about 190 nanometers, about 195 nanometers, about 200 nanometers, or more than about 200 nanometers.

Absorption peaks of various biological tissue constituents may shift with variations in temperature. The sensitivity of water fraction assessments to temperature variations may be minimized by choosing the wavelengths at which the reflectances are measured to be close to temperature isosbestic wavelengths in the water absorption spectrum. For example, wavelengths may be selected at points in the absorption spectrum where no significant temperature shift occurs. Alternately, if the degree of the temperature shift is known or may be estimated, wavelength sets may be chosen such that any temperature shift may be mathematically canceled out when optical measurements are combined to compute the value of a tissue water metric. Such wavelength sets may be selected from any one of the three primary wavelength bands (950-1400 nm, 1500-1800 nm, and 2000-2300 nm) discussed above. Wavelengths, wavelength pairs, and/or sets may, according to some specific example embodiments, be chosen from within one of these three primary bands, rather than from across these bands. For example, the wavelength pair of 1195 and 1300 nm is one such pair of temperature isosbestic wavelengths in the water absorption spectrum.

The source of near infrared light may be configured to emit one or more wavelengths. The detector may be correspondingly configured to detect reflectance transmittance or absorbtion of one or more wavelengths. Reflectance data may be converted to absorbtion data according to the Equation (2):

$$A = \log [1/R(\lambda)], \quad (2)$$

where R is the reflectance at wavelength $\lambda$. When two or more wavelengths are emitted and detected, the measured reflectances transmittances may be combined to form a single ratio, a sum of ratios, a ratio of ratios of the form $\log [R(\lambda_1)/R(\lambda_2)]$, and/or a ratio of weighted sums of $\log [R(\lambda)]$ terms, in which the numerator depends primarily on the absorbance of water, and the denominator depends primarily on the sum of the volume fractions of water, and other specific tissue constituents, such that the denominator is approximately equally sensitive to a change in the concentration of any of these specific constituents and water.

Thus, in one specific example embodiment of the present disclosure the water fraction, $f_w$ may be estimated according to the following equation, based on the measurement of reflectances transmittances, $R(\lambda)$ at two wavelengths and the empirically chosen calibration constants $c_0$ and $c_1$:

$$f_w = c_1 \log [R(\lambda_1)/R(\lambda_2)] + c_0. \quad (3)$$

As demonstrated by numerical simulations and in vitro experiments, the total tissue water fraction, $f_w^T$, may be estimated with an accuracy of approximately +/−2% over a range of water contents between 50 and 80% using Equation (3), with reflectances $R(\lambda)$ measured at two wavelengths and the calibration constants $c_0$ and $c_1$ determined empirically. Examples of suitable wavelength pairs include, but are not limited to, (a) $\lambda_1 = 1300$ nm and $\lambda_2 = 1168$ nm and (b) $\lambda_1 = 1230$ nm and $\lambda_2 = 1168$ nm.

The water fraction, $f_w$, may also be estimated according to Equation (4) below, based on the measurement of reflectances or transmittances, $R(\lambda)$ at three wavelengths and the empirically determined calibration constants $c_0$, $c_1$ and $C_2$:

$$f_w = c_2 \log [R(\lambda_1)/R(\lambda_2)] + c_1 \log [R(\lambda_2)/R(\lambda_3)] + c_0. \quad (4)$$

Better absolute accuracy may be attained using Equation (4) which incorporates reflectance measurements at an additional wavelength. The results of in vitro experiments on excised skin indicate that the wavelength triple ($\lambda_1 = 1190$ nm, $\lambda_2 = 1170$ nm, $\lambda_3 = 1274$ nm) yields accurate estimates of total tissue water content based on Equation (4).

According to some specific example embodiments, the water fraction, $f_w$ may be estimated according to Equation (5) below, based on measurement of reflectances or transmittances, $R(\lambda)$ at three wavelengths and the empirically determined calibration constants $c_0$ and $c_1$:

$$f_w = c_1 \frac{\log[R(\lambda_1)/R(\lambda_2)]}{\log[R(\lambda_3)/R(\lambda_2)]} + c_0. \quad (5)$$

The accuracy of estimates obtained using Equation (5) may be better than those attained using Equation (4), which also incorporates reflectance measurements at an additional wavelength. Numerical simulations indicate that total tissue water may be estimated to within +/−0.5% using Equation (5), where reflectances are measured at three closely spaced wavelengths: $\lambda_1 = 1710$ nm, $\lambda_2 = 1730$ nm, and $\lambda_3 = 1740$ nm. Additional numerical simulations indicate that accurate measurement of the lean tissue water content, $f_w^L$, may be accomplished using Equation (5), by combining reflectance measurements at 1125, 1185, and 1250 nm.

A tissue fluid monitor may provide a clinician with an indication of whether a patient requires more, less, or no fluid to achieve a desired state of hydration. Such a measurement may be less universally applicable than clinically desired when it is determined using an instrument that reports fractional water relative to either total body weight or total tissue content, due to the high variability of fat content across the human population. Fat contains very little water, so variations in the fractional fat content of the body lead directly to variations in the fractional water content of the body.

Gender and age-related differences in fat content reveal systematic variations in water content when averaged across many patients. This observation has been well-documented in the literature, as is shown for example in FIG. 1. Values shown in FIG. 1 have been computed from Tables II-III of Cohn et al., *J. Lab. Clin. Med.* (1985) 105(3), 305-311.

Figure 2:
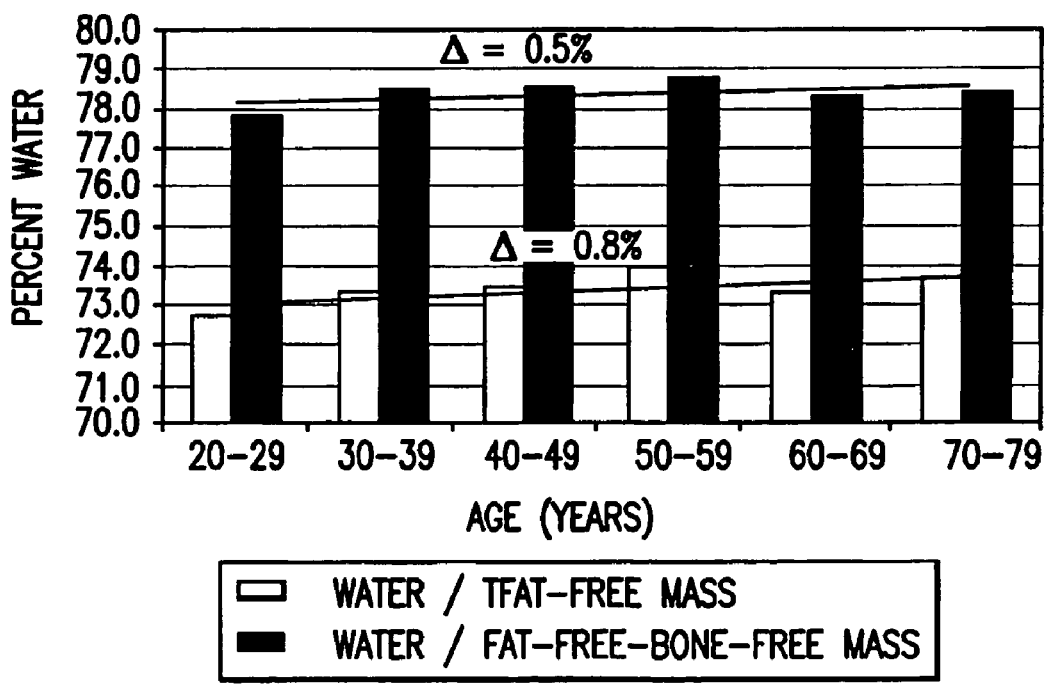
FIG. 2 is a bar graph of water content as a percentage of fat-free mass and fat-free-bone-free mass for men and women between the ages of 20 and 79.

In contrast, when fat is excluded from the calculation, the fractional water content, $f_w^L$, in healthy subjects, may be consistent across both gender and age, as shown, for example, in FIGS. 1 and 2. This suggests that $f_w^L$, may be a more clinically useful measurement than $f_w$ for certain conditions. An additional reduction in the subject-to-subject variation in the "normal" level of fractional water content may be observed if bone mass is excluded from the calculation, as may be seen in FIG. 2. This may be due to the fact that the bone content of the body tends to decrease with age (such as by osteoporosis). Thus, measurements of $f_w^L$ in tissue made using the source-detector separation, wavelength band selection, or computational algorithms of the disclosure may be closely related to whole body water content as a fraction of the fat-free-bone-free body content.

Tissue water fraction, $f_w$, may also be estimated according to the following equation, based on measurement of reflectances, $R(\lambda)$, at a plurality of wavelengths:

$$f_w = \frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}}, \quad (6)$$

where $p_n$ and $q_m$ are calibration coefficients; $R(\lambda)$ is a measure of received radiation at a wavelength; and $n=1-N$ and $m=1-M$ represent indexes for a plurality of wavelengths which may consist of the same or different combinations of wavelengths.

An obstacle to the quantification of tissue analytes may be the high subject-to-subject variability of the scattering coefficient of tissue. Determination of the fractional tissue water in accordance with Equation (6) provides an advantage in that scattering variation may be cancelled, e.g., if the N+1 wavelengths are chosen from within the same wavelength band (950-1400 nm, 1500-1800 nm, or 2000-2300 nm). An explanation of the manner in which Equation (6) cancels scattering variations is provided below.

Tissue reflectance can be modeled according to a modified form of the Beer-Lambert equation:

$$\log[R(\lambda)] = -l(\lambda) \sum_{j=1}^{J} c_j \varepsilon_j(\lambda) - \log\{I_0(\lambda)\}, \quad (7)$$

where:
R is the tissue reflectance;
l is the mean path length of light at wavelength $\lambda$;
$\varepsilon_j$ and $c_j$ are the extinction coefficients and concentration of constituent j in the tissue; and
$\log\{I_0(\lambda)\}$ is a scattering offset term.

According to this model, the scattering dependence of tissue reflectance is due to the offset term, $\log\{I_0(\lambda)\}$, and the path length variation term, $l(\lambda)$. Since the scattering coefficient varies slowly with wavelength, by selecting all of the wavelengths from within the same wavelength band, the wavelength dependence of the scattering coefficient can be ignored to a good approximation. Under these conditions, by multiplying the log of the reflectance at wavelength N+1 (or M+1) by the negative of the sum of the coefficients used to multiply the log of the reflectances at the N (or M) other wavelengths, the scattering offset terms are cancelled in both the numerator and denominator of Equation (6). This can be seen, for example, by substituting Equation (7) into the numerator of Equation (6) to obtain Equation (8):

$$\left[\sum_{n=1}^{N} p_n \log\{R(\lambda_n)\}\right] - \left[\sum_{n=1}^{N} p_n\right] \log\{R(\lambda_{N+1})\} = \quad (8)$$

$$-l \sum_{n=1}^{N} \left[p_n \sum_{j=1}^{J} c_j \varepsilon_j(\lambda_n)\right] + l\left[\sum_{n=1}^{N} p_n\right] \sum_{j=1}^{J} c_j \varepsilon_j(\lambda_{N+1}).$$

A review of Equation (8) shows that the scattering offset term has been cancelled, but the scattering dependent path length variation term, l, remains. When the numerator and denominator of Equation (6) are combined, the path length variation term is also cancelled, as shown in Equation (9):

$$fw = \frac{-\sum_{n=1}^{N} \left[p_n \sum_{j=1}^{J} c_j \varepsilon_j(\lambda_n)\right] + \left[\sum_{n=1}^{N} p_n\right] \sum_{j=1}^{J} c_j \varepsilon_j(\lambda_{N+1})}{-\sum_{m=1}^{M} \left[q_m \sum_{j=1}^{J} c_j \varepsilon_j(\lambda_m)\right] + \left[\sum_{m=1}^{M} q_m\right] \sum_{j=1}^{J} c_j \varepsilon_j(\lambda_{M+1})}. \quad (9)$$

Thus, Equation (9) depends on the concentrations and extinction coefficients of the constituents of tissue and on the calibration coefficients $p_n$ and $q_m$.

In addition to providing for variable scattering compensation, the methods using Equation (6) may allow a more general implementation by relaxing some of the constraints that may be imposed by the use of Equation (5), above. For example, to provide a certain level of accuracy for measurement of $f_w$, the numerator in Equation (5) may need to be sensitive to changes in water concentration but insensitive to changes in all other tissue constituents. More specifically, Equation (5) may require that the absorbance of all tissue constituents besides water (e.g., lipid, non-heme protein, and/or hemoglobin) are nearly equal at wavelengths 1 and 2. This constraint may be removed in Equation (6), where the coefficients $p_n$ are chosen to cancel out absorbance by all tissue constituents other than water.

In addition, to provide a certain level of accuracy for measurement of $f_w$, the denominator in Equation (5) may need to be equally sensitive to concentration changes of all tissue constituents to which the water fraction is to be normalized. In addition, Equation (5) may further require that the absorbance be equal at wavelengths 2 and 3 for all tissue constituents to be excluded from the water fraction normalization. This constraint may be removed in Equation (6), where the coefficients, $q_m$, can be chosen to cancel the absorbance contribution due to certain constituents, while equalizing the absorbance sensitivity to the remaining tissue constituents.

For fat-free water fraction measurement, the coefficients, $P_n$, in the numerator of Equation (6) may be chosen to cancel the contribution from all of the major light-absorbing constituents of tissue, except water. Similarly, the coefficients, $q_m$, in the denominator of Equation (6) may be chosen to cancel the contribution from all tissue constituents other than water and protein. In addition, the coefficients, $q_m$, may be chosen to equalize the sensitivity of the denominator to changes in water and protein on a volume fractional basis. By computing the ratio of these two terms, the result is a fractional volume measurement of water concentration in lean tissue.

In addition, application of Equation (6) to the measurement of fractional water content in total tissue volume, $f_w^T$, may be accomplished by choosing the coefficients in the denominator of Equation (6), $q_m$, so that all tissue constituents (including lipid) are equalized on a fractional volume basis.

By relaxing some of the constraints imposed by Equation (5), the use of Equation (6) may produce a more accurate prediction of fractional tissue water content, for the reasons set forth above. Various wavelength combinations may be used based on the criteria disclosed above.

Extinction coefficients of water, non-heme protein, lipid, and hemoglobin were experimentally measured to select a wavelength combination for use with Equation (6) for measuring fractional water content in lean tissue, $f_w^L$. Real tissue data were collected from 37 different volunteers at a local hospital, with Institutional Review Board (IRB) approval. The sensor measured reflected light from the pad of the finger, with a source-detector spacing of approximately 2.5 mm. The sensor was completely removed from the tissue between each pair of measurements.

Figure 3:
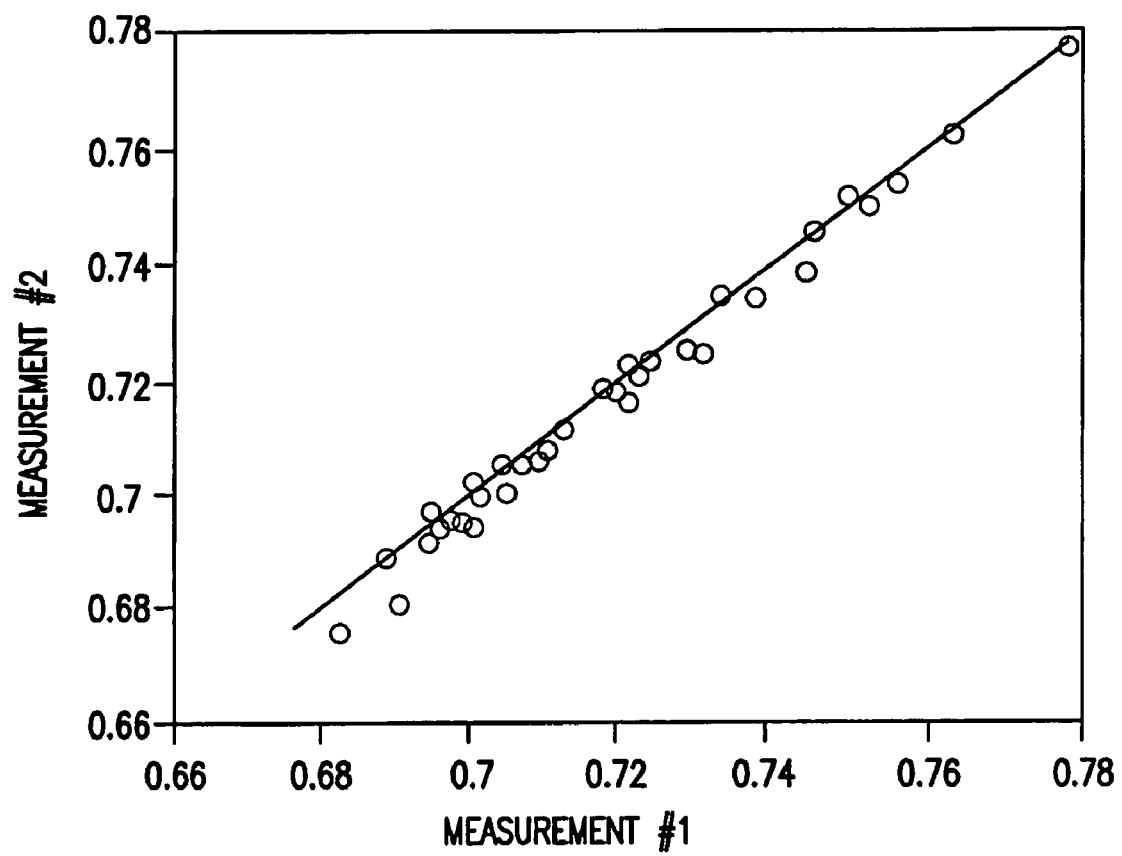
FIG. 3 is a graph of the correlation between separate fat-free or lean water fraction ("$f_w^L$") measurements on the same subject.

Various wavelength combinations were applied to a numerical model of tissue absorbance. The reproducibility of the algorithms incorporating the most promising wavelength combinations were then compared with the real tissue data. An algorithm which combines measurements at 4 wavelengths, e.g., 1180, 1245, 1275, and 1330 nm may be utilized. Using this selection of wavelengths, the measurement-to-measurement reproducibility, as shown in FIG. 3, is 0.37%, indicating high reproducibility of the tissue water measurements using the methods disclosed herein.

In addition to providing a method for measuring tissue water fraction, the method in accordance with Equation (6) above, may also have general utility for the fractional quantification of analytes in tissue. By appropriate choice of wavelengths and coefficients, Equation (6) may be extendible to the fractional concentration measurement of any tissue constituent or combination of constituents in tissue with respect to any other constituent or combination of constituents. For example, this equation also may be applicable for the determination of the fractional hemoglobin content in tissue.

Thus, according to one specific example embodiment, the present disclosure provides a method of assessing the fractional volume of total hemoglobin in tissue, including measuring reflectance at wavelengths strongly absorbed by hemoglobin, measuring reflectance at wavelengths absorbed, e.g., strongly absorbed, by remaining tissue constituents (such as water, lipid, and/or non-protein), entering these measurements in Equation (6), and calculating the fractional volume of total hemoglobin in tissue. The coefficients, $p_n$, in the numerator of Equation (6) may be chosen to cancel the absorbance contributions from all tissue constituents except total hemoglobin. The coefficients, $q_m$, in the denominator of Equation (6) are chosen to equalize the absorbance contributions of all major tissue constituents, on a volume fractional basis. One example of a specific wavelength combination for accomplishing this measurement may be 805 nm, 1185 nm, and 1310 nm. At 805 nm the absorbance by the oxy- and deoxyhemoglobin are approximately equal. At 1185 nm, the absorbance of water, non-heme protein, and lipid, are nearly equal on a fractional volume basis. At 1300 nm the tissue absorbance may be dominated by water.

According to yet another specific example embodiment of the present disclosure, measurement of fractional concentrations of different species of hemoglobin in tissue may be performed. In general, the method provides a means of measuring the fractional concentration of hemoglobin in a first set comprised of one or more species of hemoglobin with respect to the concentration of hemoglobin in a second set comprised of one or more hemoglobin species in tissue. The coefficients, $p_n$, in the numerator of Equation (6) may be chosen to cancel the absorbance contributions from all tissue constituents except the hemoglobin species included in set 1. The coefficients, $q_m$, in the denominator of Equation (6) may be chosen to equalize the absorbance contributions from all tissue constituents except the hemoglobin species included in set 2. Sets 1 and 2 are subsets of hemoglobin species that are present in the body tissue or blood. For example, such hemoglobin species include oxyhemoglobin, deoxyhemoglobin, carboxyhemoglobin, methemoglobin, sulfhemoglobin and, so on. And in general, as used herein, other physiological parameters have other subsets of constituents each being capable of absorbing at different wavelengths. When set 1 is comprised of oxyhemoglobin and set 2 is comprised of oxy- and deoxyhemoglobin, an example of a specific wavelength combination for accomplishing the measurement may be 735, 760, and 805 nm.

Individuals of ordinary skill in the art will recognize that additional terms may be added to Equations (3)-(6) with the guidelines of the present disclosure. These additional terms may be used to incorporate reflectance measurements made at additional wavelengths and, thus, e.g., possibly further improve accuracy.

According to an additional specific example embodiment, the disclosure provides methods for quantitative assessment of fluid shifts into and/or out of the bloodstream using spectrophotometry. Without being limited to any particular mechanism of action, this specific example embodiment recognizes that pulsations caused by expansion of blood vessels in the skin as the heart beats produce changes in the reflectance at a particular wavelength. These changes may be proportional to the difference between the effective absorption of light in the blood and the surrounding interstitial tissues. Numerical simulations indicate that, if wavelengths are chosen at which water absorption is sufficiently strong, the difference between the fractions of water in the blood, $f_w^{IV}$ and surrounding tissue, $f_w^{EV}$ may be proportional to the ratio of the dc-normalized reflectance changes ($\Delta R/R$) measured at two wavelengths, according to Equation (10) below:

$$f_w^{EV} - f_w^{IV} = c_1 \frac{(\Delta R/R)\lambda_1}{(\Delta R/R)\lambda_2} + c_0$$

where $c_0$ and $c_1$ are empirically-determined calibration constants. This difference, integrated over time, provides a measure of the quantity of fluid that shifts into and/or out of the capillaries.

Some specific example embodiments of the disclosure provide methods of assessing a water balance index, Q, using Equation (11):

$$Q = \frac{f_w^{IV} - f_w^{EV}}{f_h^{IV}} = a_1 \frac{(\Delta R/R)_{\lambda 1}}{(\Delta R/R)_{\lambda 2}} + a_0, \quad (11)$$

wherein $f_h^{IV}$ is the fractional volume concentration of hemoglobin in the blood; and $a_0$ and $a_1$ are calibration coefficients.

The use of Equation (11) to determine a water balance may be similar to using Equation (10) above, where $f_h^{IV}$ is set equal to 1. However, using Equation (10) may yield a more accurate determination by not neglecting the influence of $f_h^{IV}$ on the derived result. The effect of this omission may be understood by allowing total hemoglobin to vary over the normal physiological range and computing the difference between the results provided by Equation (10) when $f_h^{IV}$ is fixed or allowed to vary. For example, when calculations were performed with $f_w^{Iv}$ varying between 0.75 and 0.80 and $f_h^{IV}$ varying between 0.09 and 0.135, the resulting error was as large as +/−20%. In situations of extreme blood loss or vascular fluid overload (hypo- or hypervolemia), the error may be larger.

The index provided by Equation (10) may have clinical utility without further manipulation. For example, simultaneous measurement of both Q and fractional tissue water (either $f_w$ or $f_w^L$) may directly and/or indirectly provide a clinical indication of changes in both volume and osmolarity of body fluids. Alternatively, the index (Q) may be combined with a separate measurement of fractional hemoglobin concentration in blood, $f_h^{IV}$, (such as may be provided by standard clinical measurements of hematocrit or total hemoglobin) to provide a measure of the difference between the intravascular and extravascular water content, $f_w^{IV}-f_w^{EV}$.

Table 1 lists 6 examples of combinations of volume and osmolarity changes in body fluids that are clinically observed (from Physiology, 2$^{nd}$ Edition, Linda S. Costanzo, Williams and Wilkins, Baltimore, 1998, pg. 156), and the expected direction and magnitude of the resultant change in fractional volume of water in blood ($f_w^{IV}$), the fractional volume of water in tissue ($f_w^{EV}$), the fractional volume of hemoglobin in blood ($f_h^{IV}$), the numerator of Q ($Q_n$), the inverse of the denominator of Q ($1/Q_d$), the combined result ($Q_n/Q_d=Q$), and the fractional volume of water in lean tissue, $f_w^L$.

For example, is-osmotic volume expansion (e.g., expansion induced by infusion with isotonic saline) may result in an increase in the fraction of water in blood ($f_w^{IV}$), a small increase in the extravascular water fraction ($f_w^{EV}$), and/or a large decrease in the fractional concentration of hemoglobin in the blood ($f_h^{IV}$). The combined effect of these 3 factors would result in a large increase in Q. A small increase in the fraction of water in the lean tissue, $f_w^L$, would also be expected.

When Q and $f_w^L$ are viewed in combination, they provide unique signatures for each of the 6 types of fluid balance change listed in Table 1. An instrument providing these measurements in a non-invasive and/or continuous fashion provides a powerful tool for the monitoring of tissue water balance.

TABLE 1

Expected Changes in Q and $f_w^L$ Resulting from Changes in Body Fluid Volume and Osmolarity

| Type | Example | $f_w^{IV}$ | $f_w^{EV}$ | $f_h^{IV}$ | $Q_n$ | $1/Q_d$ | Q | $f_w^l$ |
|---|---|---|---|---|---|---|---|---|
| Isosmotic volume expansion | Isotonic NaCl Infusion | ↑ | ↑ | ↓ | ↑ | ↑ | ↑ | ↑ |
| Isosmotic volume contraction | Diarrhea | ↓ | ↓ | ↑ | ↓ | ↓ | ↓ | ↓ |
| Hyperosmotic volume expansion | High NaCl intake | ↑ | ↓ | ↓ | ↑ | ↑ | ↑ | ↑ |
| Hyperosmotic volume contraction | Sweating, Fever | ↓ | ↓ | ↑ | 0 | ↓ | ↓ | ↓ |
| Hypo-osmotic volume contraction | SIADH | ↑ | ↑ | ↓ | 0 | ↑ | ↑ | ↑ |
| Hypo-osmotic volume contraction | Adrenal Insufficiency | ↓ | ↓ | ↑ | ↓ | ↓ | ↓ | ↓ |

Extracellular Fluid Assessment

Water may move from one compartment to another. For example, extracellular water may move from place to place within the body in response to gravity or hydrostatic pressure. In addition, water content may change independently in the intracellular, interstitial, and/or vascular compartments, with different implications for fluid management. For instance, an overload of interstitial water may lead to water in the lungs, impairing gas exchange. Of the two extravascular compartments, the interstitial volume may be about three times greater than the vascular volume. In view of some dynamics of water movement, measurement of water in a single tissue or compartment may not correlate well with total body water. For example, lean water fraction ($f_w^l$) measurements may read high relative to whole-body $f_w^l$ if the sensor is on a site that is significantly below the heart and/or, reciprocally, may read low if the sensor is on a site that is significantly above the heart.

Therefore, the present disclosure provides, in some specific example embodiments, methods for accounting for and/or assessing such mobile constituents. For example, a body-fluid metric may be assessed by determining the difference between the lean water fraction of a tissue of interest and a reference tissue. A reference tissue may be the same tissue under a different hydrostatic pressure or a different tissue. For example, a single sensor may be placed in a single tissue and a body fluid, e.g., water, metric assessed. Then the hydrostatic condition of the location may be changed before a second assessment of the body fluid-related metric. To minimize unstable or artifactual readings, the tissue may be given time to re-equilibrate before assessing the same site a second time.

The hydrostatic condition of an assessment site may be changed by any means available in the art. For example, the hydrostatic condition may be altered, e.g., by changing the position of the site relative to the rest of the body, such as, e.g., by raising or lowering the sampling location relative to the subject's heart. Alternatively, the hydrostatic condition may be altered by increasing or reducing the ambient external pressure on a location. This may be accomplished, e.g., by applying pressure to a site during the first or second assessment using a tissue compressor, e.g., compression weight, cuff, belt or pressure chamber.

Thus, some specific example embodiments of the present disclosure relate to a method for evaluating changes in extracellular fluid volume, including: (a) measuring optical signals, e.g., sets of optical signals, at one or more wavelengths, received by at least one optical detector from at least one light source at an assessment site or sites having a first hydrostatic pressure; (b) measuring optical signals, e.g., sets of optical signals, at one or more wavelengths, received by at least one optical detector from at least one light source at a tissue site or sites having a second hydrostatic pressure; (c) estimating fluid content, e.g., water content, from said optical signals acquired from said site and/or sites having said hydrostatic pressures; and (d) determining the relationship of said water-content estimates to the differences in hydrostatic pressure and estimating changes in extracellular fluid volume based on said relationship.

In some specific example embodiments, the amount of extracellular water in a tissue may be assessed by determining the difference between the lean water fraction of that tissue and a reference tissue. The reference tissue may be the same tissue under different hydrostatic or gravitational pressure. For example, extracellular water may be expressed as a fraction of the total water present (e.g., a sum of intracellular and extracellular water) as shown in Equation (13):

$$f_w^{EC} = \frac{C_w^{EC}}{C_w^{IC} + C_w^{EC}}, \quad (13)$$

wherein
$C_w^{IC}$ is the concentration of intracellular water; and
$C_w^{EC}$ is the concentration of extracellular water.

Thus, where $$Z = \left[\sum_{n=1}^{N} p_n \log\{R(\lambda_n)\}\right] - \left[\sum_{n=1}^{N} p_n\right] \log\{R(\lambda_{N+1})\}, \quad (14)$$

with terms defined as in Equation 6, extracellular water may be assessed by measuring Z at equilibrium ($Z_{eq}$), measuring Z under pressure ($Z_p$), and computing $f_w^{EC}$ according to Equation 15:

$$f_w^{EC} = 1 - \frac{Z_p}{Z_{eq}}. \quad (15)$$

Equation 15 may apply where the coefficients, $p_n$, or Z are chosen to cancel out absorbance by all tissue constituents other than water. In some specific example embodiments, assessment of a fraction of extracellular water relative to total water in a sampled volume may provide a direct assessment of edema in the effected volume. Reflectance measurements in several regions of the spectrum may be mathematically combined in some embodiments so that the contributions due to all constituents except water are cancelled. Measurements may be performed before and after application of pressure at a tissue site. By computing a ratio of results with and without applied pressure, an extracellular water fraction may be estimated.

The extracellular water fraction may also be equal to the change in total water fraction. Measurements of extracellular water may be obtained by raising the pressure at the site until no further changes in the total or lean water fraction are observed. The total or lean water fraction value at this peak pressure may be substantially equal to the intracellular water fraction. If the residual water is not negligible in a particular tissue, a constant may be used to correct for the small amount of remaining extracellular water. Such a constant may be chosen or empirically-determined by those of ordinary skill in the art.

The reference tissue, alternatively, may be a different tissue site ("$S_{ref}$"). The site of interest and the reference site may be independently chosen. In some specific example embodiments of the disclosure, assessments at each location may be made at different times, at about the same time, and/or at the same time. The reference tissue may be within the same or similar tissue or organ or may be within a different tissue or organ. In some specific example embodiments, the reference tissue may be in hydrostatic contact with the site of interest ("$S_i$"), such that mobile extracellular water may move between the two. If the extracellular water at the site of interest moves into the reference site upon the application of pressure, the change in the total water fraction or lean water fraction at the reference site may be correlated with the resting extracellular water content at the site of interest ($f_{w(Si)}^{EC}{}_{(eq)}$). If the amount of pressure applied at the site of interest is increased until no further changes in total water at the reference site are observed, the extracellular water at the site of interest may be assessed using Equation (16):

$$f_{w(S_i)}^{EC(eq)} = e_0 \left[1 - \frac{Z_p}{Z_{eq}}\right], \quad (16)$$

wherein
$e_0$ is a correlation constant;

The correlation constant may have a value of one (1) when all of the water that moves out of the site of interest moves into the reference site. If less than the entire amount of extracellular water at the site of interest moves into the reference site, the value of $e_0$ will be greater than one and may be calculated and/or empirically-determined. This may be the case when, for example, mechanical pressure affects the flow of water out of the tissue site of interest and/or into the reference site. In specific example embodiments where the extracellular water at the site of interest moves radially into adjacent tissue upon the application of pressure, the correlation constant may be a function of the radial distance from the site of interest to the reference site. If the size and/or shape of the area into which the extracellular water moves is unknown, a grid centered on the site of interest may be drawn and total or lean water measurements made in each section as pressure is increased.

According to some non-limiting specific example embodiments, the reference site need not be in hydrostatic contact with the site of interest. For example, water may not directly move between a site of interest and a reference site when the water status of one may be communicated to and impacts the water status of the other site via hormonal, electrical, and/or other signals. In some specific example embodiments, there may be no connection between the tissue site of interest and the reference site.

Accumulation of extracellular water may be monitored for diagnostic or therapeutic purposes. For example, an excessive amount of extracellular water in a tissue may increase the presence of edema in that tissue. A subject confined to a bed for an extended period of time may accumulate extracellular water in tissues at or near the surface of the bed. Extracellular water accumulation may be monitored by periodically measuring the total and/or lean water content of a tissue above the subject's center of mass, periodically measuring the total and/or lean water content of a tissue below the subject's center of mass, and calculating the difference between the two. Over time, gravity may drain extracellular water from the upper tissues into the lower tissues. Extracellular water at the lower site ($S_{low}$) may be estimated using Equation 17:

$$f_{w(Slow)}^{EC} = k_0 \left[ 1 - \frac{Z_p}{Z_{eq}} \right], \tag{17}$$

wherein
$k_0$ is a correlation constant;

The correlation constant ($k_0$) may be empirically determined and may correct for incomplete drainage from $S_{up}$ to $S_{low}$. Extracellular water may be a useful metric for determining when to turn over a subject who is partially or completely immobile (e.g., a coma patient) to reduce or prevent bed sores or infections. Thus, when the extracellular water content of the upper tissue falls below a given threshold or the content of the lower tissue exceeds a given threshold, the subject may be moved to redistribute the extracellular water.

According to some specific example embodiments, the disclosure provides methods of assessing the extracellular water in tissue that may be diseased and/or damaged. In such tissue, there may be a risk that application of pressure would aggravate the already poor condition of the tissue. Two or more detectors may be placed around the site of interest. The site of interest may be placed in a pre-selected position relative to the heart or the whole-body center of mass. Alternatively, if the site of interest is in an extremity, it may be positioned relative to the center of mass of that extremity. Positioning relative to a mass or circulatory reference point may be performed to minimize changes in hydrostatic pressure at the site of interest. A water metric may then be assessed at the site of interest by measuring the water metric at the reference site(s) where detectors may be located, processing this information together with the position of the site of interest relative to the detectors, heart, and/or center of mass, and calculating the metric at the site of interest. The water fraction at any of the detector sites, the change in fractional water between sites, and/or the rate of change in fractional water between sites may be used alone or in combination to assess water status of the diseased and/or damaged tissue. By placing an array of detectors at varying distances from the trauma site and assessing a body-fluid metric at each, it may be possible to determine whether and/or how much fluid is being lost or gained through a wound site. In some of these embodiments, it may be desirable to take precautions against contaminating the site. For example, a water probe and/or detector may further comprise at least one sanitized and/or sterilized surface proximal to a portion of the probe and/or detector that may be expected to be in close proximity to the site.

Fluid Assessment with Location Information

Additional specific example embodiments of the disclosure are provided in which a single-site fluid metric assessment may be combined with site location information to calculate or estimate the corresponding whole-body fluid metric. The location of the assessment site may be directly and/or indirectly detected or determined. Alternatively, the location of the device used to assess the body fluid metric (the "water probe") may be used. Location information may include the position, orientation, and/or elevation of the assessment site and/or the water probe relative to the subject's center of mass and/or some other bodily reference point. Location information may also include position, orientation, and/or elevation of the assessment site and/or of the water probe relative to any reference point such as, e.g., the subject's bed, the ground, the gravitational vector, and/or combinations thereof. Location information may be assessed using an water probe location sensor. Location information may be used to determine (a) a multiplier (e.g., a correlation constant) and/or (b) an operation to perform on the single-site data to produce the corresponding whole-body metric.

One of ordinary skill in the art will recognize that multiple means for sensing position, orientation, and/or elevation changes are readily available. For example, orientation sensors may be used that are like sensors integrated into flat-panel displays, including those of handheld medical monitors, for the purpose of switching the display from portrait to landscape mode. Means of determining elevation changes relative to the heart might include settings on the surgical table or hospital bed, a camera, a small tube with fluid and a pressure sensor at one end. In addition, an water probe location sensor according to some specific example embodiments of the disclosure may include one or more mechanical linkages, such as, e.g., an arm with a joint, that attaches to a probe. In these cases, the position and/or orientation of a probe may be ascertained from the length of the arm, the angle of its joint, and/or the position of the subject. Remote water probe location sensors may also provide location information relative to the subject's body, such as, e.g., where a sensor uses optical and/or ultrasound emitters (e.g., on the probe, subject, and/or hospital bed) and detectors (e.g., on the sensor). Alternatively, a sensor may include a video camera and/or may use object recognition image processing software to detect probe location and/or tissue site position, orientation, and/or elevation. In yet another example, a sensor may also receive signals from one or more small piezoelectric vibratory gyroscopes located in a probe. These may be the same types of gyroscopes that may be used in automobile navigation systems and may allow detection of probe location information.

According to a specific example embodiment of the present disclosure, a water probe and a water probe location sensor may be in direct contact, e.g. physical contact, such that probe and sensor may be integrated into a single unit. If so, location information may be assessed with reference to external points, e.g., the subject's hospital bed, the floor, and/or the walls. Emitters and/or detectors may be placed in these external locations as needed. According to another specific example embodiment of the disclosure, probes and sensors may also be physically connected by an arm, cable, and/or other linker. Alternatively, probes and sensors may lack any direct connection. Where a probe and a sensor are discontiguous, each may be configured to exchange signals with the other, send signals to a display, send signals to a remote processor, and/or combinations thereof.

Thus, the present disclosure contemplates detecting a location of a probe and/or compensating for overly high or low body-fluid metrics assessed in, e.g., a tissue. Determining the nature and/or magnitude of that compensation may include collection and/or analysis of data from human volunteers placed in various positions for reasonable lengths of time with sensors at tissue sites. Accordingly, the disclosure further provides specific example embodiments wherein a database of body-fluid metric data from a variety of body locations with the body in a variety of positions may be compiled in relation to an individual and/or population. The total body water metric in an individual, according to a specific example embodiment of the disclosure, may then be assessed by detecting a body-fluid metric at an assessment site, identifying the location of the assessment site on the body, identifying the location of the assessment site relative to a center of mass and/or circulatory reference point, and/or correlating the local body-fluid metric and/or location data with the corresponding whole body-fluid metric.

Systems and Devices

In some specific example embodiments, the present disclosure provides systems and devices for measuring a body-tissue fluid content metric, e.g., water content. Systems and/or devices for assessing whole-body water content of a subject may include a local water content probe (e.g., a water probe) configured to assess a local fluid metric at a tissue site (e.g., a tissue site of interest and/or a tissue reference site). A system, device, and/or probe of the disclosure may include, in some embodiments, a reflectance standard (e.g., a teflon block) to calibrate out the wavelength response or sensitivity or emissivity of tissue site emitters and/or detectors. A system and/or device of the disclosure may include, in some embodiments, a probe receiver configured to contact an area at or near a tissue site and configured to releasably engage a probe and/or probe housing. For example, a probe receiver may include an toroidally-shaped adhesive pad that encircles a tissue site when positioned on a subject and receives a probe or probe housing into its center space.

Systems and/or devices of the disclosure may also include a tissue compressor configured to alter (e.g., increase or decrease) the hydrostatic pressure of an assessment site and/or a reference site. Systems and/or devices of the disclosure may further include a probe location information sensor configured to determine location information of a probe and/or an assessment site. Systems and/or devices according to the disclosure may further include a processor, e.g., a processing device, configured to process a local fluid content metric at a tissue site of interest and a local fluid content metric at a tissue reference site to produce a whole-body fluid content metric. In other specific example embodiments, systems and/or devices according to the disclosure may further include a processor, e.g., a processing device, configured to process a local fluid content metric and probe location information to produce a whole-body fluid content metric. According to some specific example embodiments, at least a portion of a system or device of the disclosure may be configured to be sterile, sanitizable, disposable, replaceable, and/or repairable. In other specific example embodiments, at least a portion of a system and/or device, e.g., a probe, may be covered with a disposable cover. For example, a probe may be covered in whole or in part by a hygienic cover similar to those used with infrared ear thermometers.

Systems and/or devices of the disclosure may be configured to assess a local fluid metric by any means available including, without limitation, bioimpedance, transepidermal water loss, viscoelastic measurements, optical spectrophotometry, magnetic resonance, ultrasound, and/or combinations thereof. For example, bioimpedance analysis and/or bioelectrical impedance spectroscopy may be used to apply an electrical current to assess tissue conductivity and, thereby, obtain a local fluid metric. It may be based, at least in part, on the different conductive and dielectric properties of various biological tissues at various biological tissues at various frequencies of current. An applied electrical current may follow a path of least resistance. In tissues a path of least resistance may be extra-cellular fluid or cells themselves depending on their conductivity, e.g., blood, muscle, and/or other fat free tissues.

For example, the disclosure provides systems, devices, and/or methods for assessing a whole body fluid metric using bioimpedance analysis and/or bioelectrical impedance spectroscopy. In one specific example embodiment, a method for assessing a whole body fluid metric may include applying an electrical current to a tissue site, assessing the tissue site conductivity, obtaining tissue site location information, and processing the tissue site conductivity and location information to produce a whole body fluid metric. Assessing tissue site conductivity may include contacting at least a portion of a subject with two or more electrical contacts, applying a known current at one or more frequencies through the at least two electrical contacts and measuring impedance between the at least two electrical contacts.

The disclosure also provides, in some specific example embodiments, a system and/or device for assessing a whole body fluid metric. The system may include a disposable bioimpedance water probe, a processing device (e.g., a processor), and/or a location sensor. The system may further include a power source (e.g., an alternating current source), one or more controls (e.g., a rheostat), and/or one or more safety mechanisms (e.g., a current governor). A bioimpedance water probe may include two or more electrical contacts configured for electrically contacting and applying a current to at least a portion of a subject.

In addition, systems and/or devices may be designed to make measurements using optical spectrophotometry. A device may include a probe housing configured to be placed near and/or at an assessment site; light emission optics connected to the housing and configured to direct radiation at the assessment site; and/or light detection optics connected to the housing and configured to receive radiation from the assessment site. A system may include a probe housing configured to be placed near and/or at an assessment site; light emission optics connected to the housing and configured to direct radiation at the assessment site; light detection optics connected to the housing and configured to receive radiation from the assessment site; a processing device, e.g., a processor, configured to process radiation from the light emission optics and the light detection optics to compute the metric; and/or a display on which raw data and/or the body-fluid metric may be displayed. The display may be operably coupled to light emission optics, light detection optics, and/or a processor. A device, e.g., a probe housing, may include a pressure transducer to assess the compressibility of tissue for deriving an index of a fraction of free water within said tissue.

According to some specific example embodiments, systems and/or devices may include a light source capable of emitting electromagnetic radiation of at least one wavelength. For example, systems and/or devices may include a light source that emits a broad or narrow band of wavelengths of infrared, visible, and/or ultraviolet light. The light source may also emit fluorescent or phosphorescent light. A light source may emit light continuously, intermittently and/or sporadically. In some specific example embodiments, systems and/or devices may include any additional spectrophotometry components including, without limitation, one or more modulators, polarizers, rhombs, etalons, prisms, windows, gratings, slits, interferometers, lenses, mirrors, reflective phase retarders, wavelength selectors, waveguides, beam expanders, beam splitters, and/or photodetectors.

Some specific example embodiments of the disclosure may be understood by reference, in part, to FIGS. 4A-5C, wherein like numbers refer to same and like parts. These figures are illustrative only and are not intended to limit the possible sizes, shapes, proportions, and/or relative arrangements of various specific example embodiments. Table 2 lists reference numerals with their associated names and figures in which they appear.

Figure 4A:
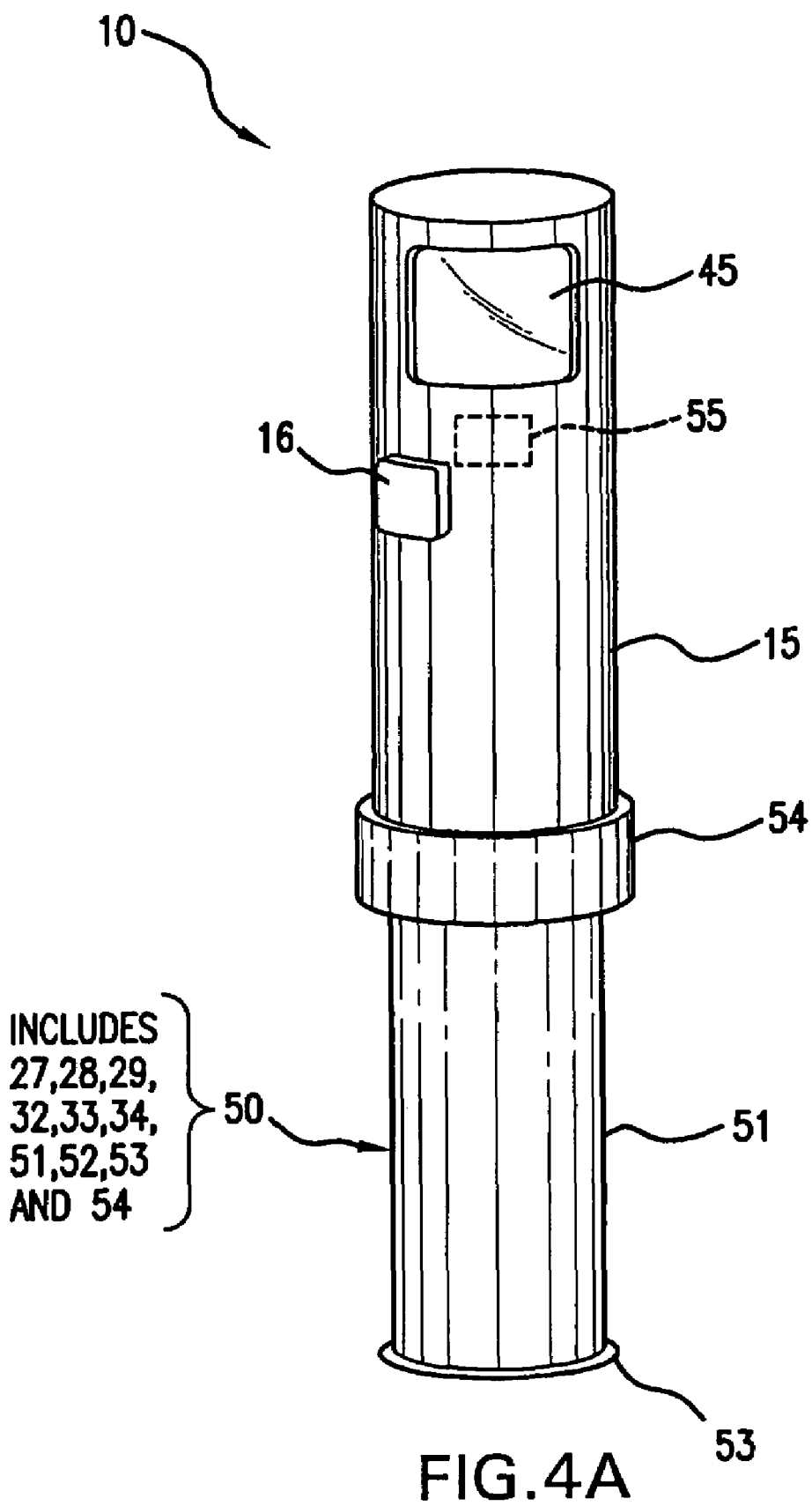
FIG. 4A shows an isometric view of one example of a system with a disposable water probe in an engaged position according to the teachings of the present disclosure.
Figure 4B:
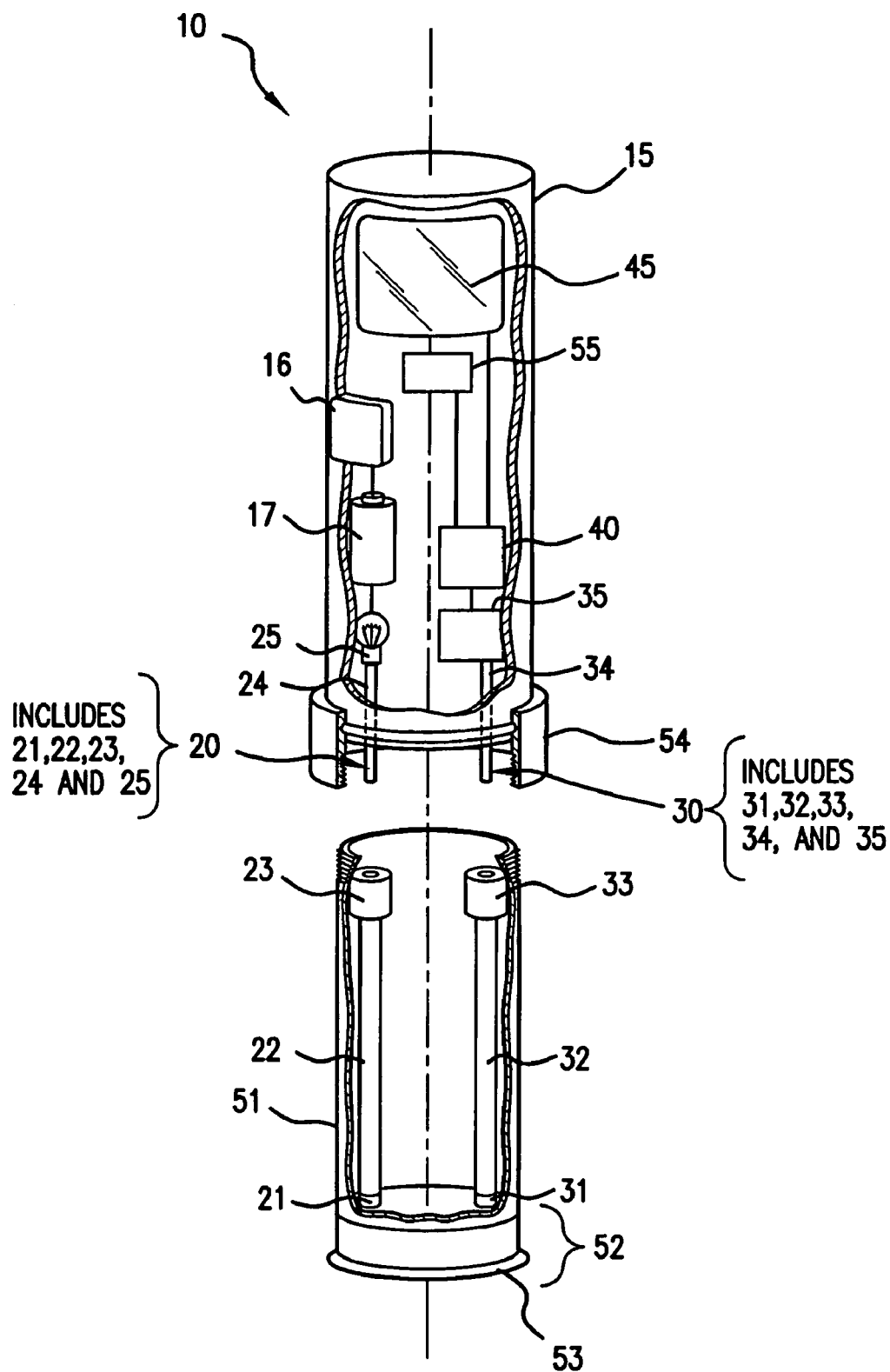
FIG. 4B shows a cut-away view of the water assessment system of FIG. 4A with the disposable water probe in a disengaged position.

In the non-limiting specific example embodiment shown in FIGS. 4A-4B, system 10 may include system housing 15, light emission optics 20, light detection optics 30, processor 40, display 45, disposable water probe 50, and water probe location sensor 55. Light emission optics 20 may include light emission aperture 21, disposable fiber optic cable 22, fiber optic cable connector 23, fiber optic cable 24, and light source 25. Light detection optics 30 may include light detection aperture 31, disposable fiber optic cable 32, fiber optic cable connector 33, fiber optic cable 34, and light detector 35.

Radiation may be conveyed by light emission optics 20 to the tissue site. For example, light emission optics 20 may be configured such that up to the entire amount of radiation emitted by light source 25 enters fiber optic cable 24, passes through fiber optic cable connector 23, disposable fiber optic cable 22, and aperture 21, and contacts the tissue site. Similarly, radiation may be conveyed by light detection optics 30 from the tissue site to light detector 35. For example, light detection optics 30 may be configured such that up to the full amount of radiation reflected, scattered, and/or transmitted by a tissue site may enter light detection aperture 31 and pass through disposable fiber optic cable 32, fiber optic cable connector 33, and fiber optic cable 34 and contact at least a portion of light detector 35.

System 10 may also include components (now shown) for dispersing a broad band source into constituent wavelength, e.g. a prism, grating, interferometer, band-pass filters, tunable filters.

Detector 35 may be configured to detect the amount and/or wavelength(s) of light received from a tissue site. Light detector 35 may deliver a signal corresponding to the light detected to operably coupled processor 40. Light emission optics 20 may be configured to deliver to processor 40 a signal corresponding to the amount and/or wavelength of light delivered to the tissue site. Processor 40 may be configured to perform one or more mathematical operations on the signals received. Processor 40 may further be configured to deliver to display 45 a signal corresponding to mathematical operation(s) performed, data used in performing mathematical operation(s), and/or results of the mathematical operation(s). Display 45 may also receive from any system component signals corresponding to the amount and/or wavelength of light (a) emitted by light source 25, (b) delivered to the tissue site by light emission optics 20, (c) received by light detection optics 30, and/or (d) detected by detector 35.

System 10 may also include water probe location sensor 55. Sensor 55 may be configured to detect and/or receive location information. Location information may include the location and/or orientation of at least a portion of system 10, the location and/or orientation of the site of assessment, and/or the location and/or orientation of a reference point. Sensor 55 also may be configured to deliver a signal corresponding to location information to processor 40.

Disposable water probe 50 may include aperture 21, disposable fiber optic cable 22, fiber optic cable connector 23, aperture 31, disposable fiber optic cable 32, fiber optic cable connector 33, disposable water probe housing 51, spacer 52, and/or seal 53. Spacer 52 may be a separate component of probe 50. Alternatively, it may be formed simply by extending the walls of probe housing 51 a desirable distance beyond light emission aperture and/or light detection aperture.

Disposable water probe 50 may be configured to be replaced, reconditioned, repaired, sanitized, and/or sterilized between each use. Disposable water probe 50 may also be configured to contact a subject at or near seal 53. Seal 53 may be configured to create a light-tight seal between probe housing 51 and a tissue site. In this context, light-tight means that up to all extraneous light is excluded from the tissue site to permit detection of at least a portion of the light source light reflected, scattered, absorbed, and/or transmitted by the tissue site.

Figure 5B:
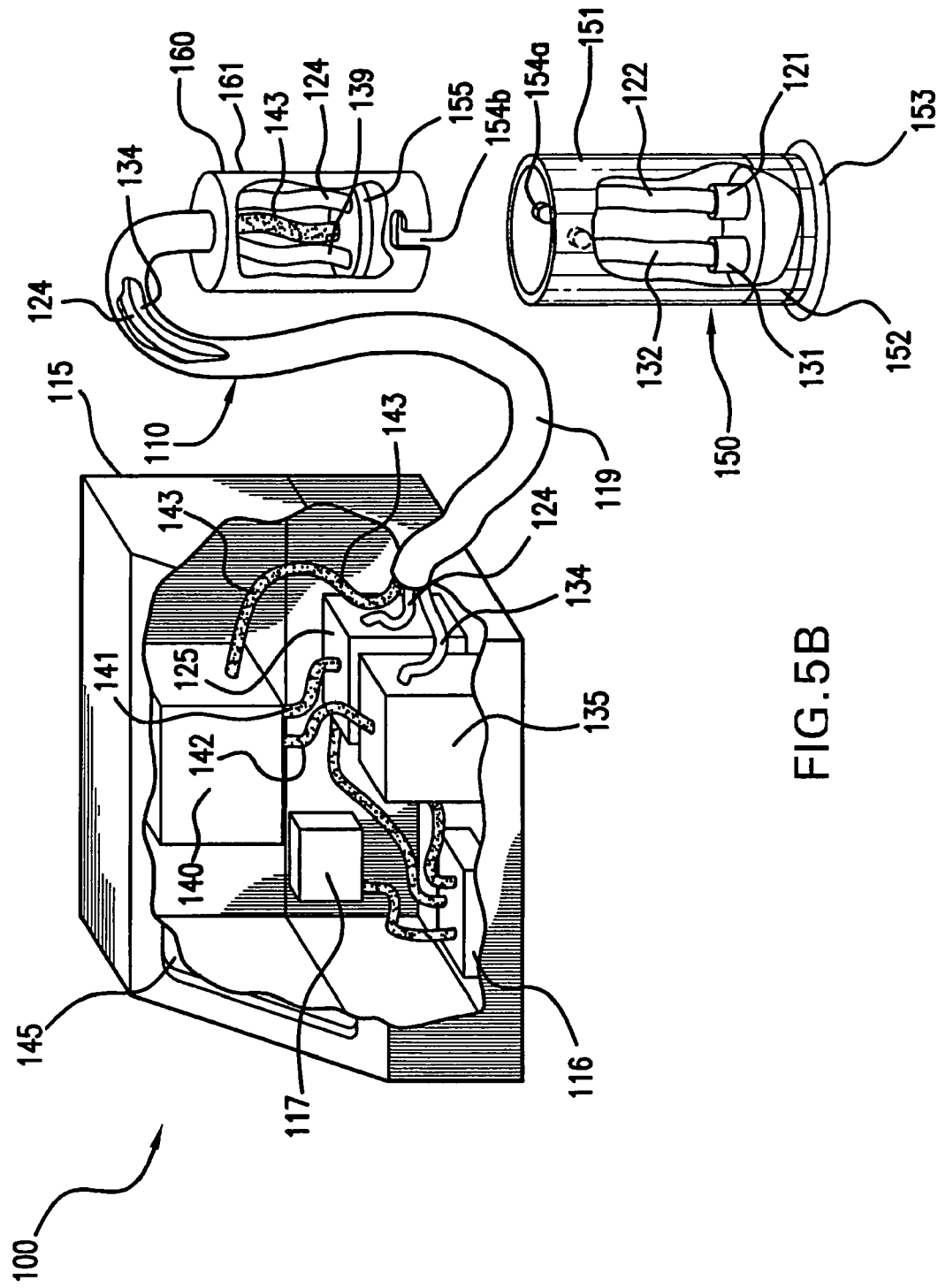
FIG. 5B shows a cut-away view of the system of FIG. 5A with the disposable water probe in a disengaged position.
Figure 5C:
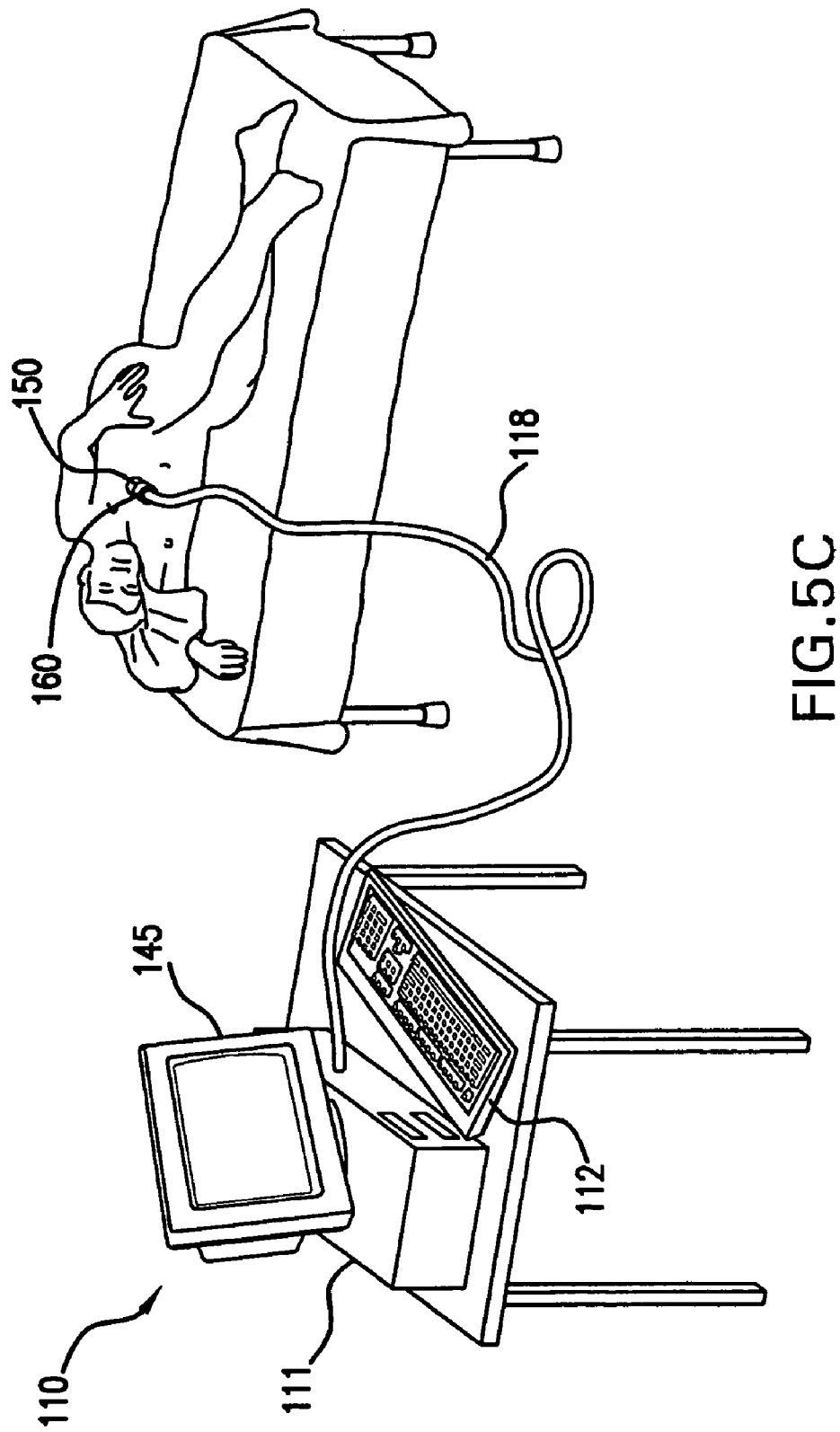
FIG. 5C shows an isometric view of a variation of a system of FIG. 5A in which the monitor is separate from the base unit and the disposable water probe is in contact with the mid-line of the torso of a subject.

According to the specific example embodiment shown in FIG. 5A, system 110 may include base unit 111, optical fiber bundle 118, disposable water probe 150, and reusable water probe manipulator 160. Base unit 111 may include housing 115, controller 116, power inlet or power source 117, optical fiber bundle 118, optical fiber bundle housing 119, at least a portion of fiber optic cable 124, light source 125, at least a portion of fiber optic cable 134, light detector 135, and processor 140 as shown in FIG. 5B. Base unit 111 may further include display 145 as an integral or separate component as shown respectively in FIGS. 5B and 5C. Base unit 111 may additionally include a user input such as, e.g., keyboard 112, as shown in FIG. 5C.

Base unit 111 may be connected to disposable water probe 150 by reusable water probe manipulator 160 and optical fiber bundle 118. The length of optical fiber bundle 118 may be selected in accordance with the use contemplated, the strength of the light source, the presence and size of apertures, the transmittance of fiber optic cables, and/or the sensitivity of the detector.

Light emission optics 120 may include light emission aperture 121, disposable fiber optic cable 122, fiber optic cable connector 123, fiber optic cable 124, and light source 125. Light detection optics 130 may include light detection aperture 131, disposable fiber optic cable 132, fiber optic cable connector 133, fiber optic cable 134, and light detector 135.

System 110 may also include components (now shown) for dispersing a broad band source into constituent wavelength, e.g. a prism, grating, interferometer, band-pass filters, tunable filters.

Radiation may be conveyed by light emission optics 120 to the tissue site. For example, light emission optics 120 may be configured such that up to the entire amount of radiation emitted by light source 125 enters fiber optic cable 124, passes through fiber optic cable connector 123, disposable fiber optic cable 122, and aperture 121, and contacts the tissue site. Similarly, radiation may be conveyed by light detection optics 130 from the tissue site to light detector 135. For example, light detection optics 130 may be configured such that up to the full amount of radiation reflected, scattered, and/or transmitted by a tissue site may enter light detection aperture 131 and pass through disposable fiber optic cable 132, fiber optic cable connector 133, and fiber optic cable 134 and contact at least a portion of light detector 135.

Detector 135 may be configured to detect the amount and/or wavelength(s) of light received from a tissue site. Light detector 135 may deliver a signal corresponding to the light detected to operably coupled processor 140. Light emission optics 120 may be configured to deliver to processor 140 a signal corresponding to the amount and/or wavelength of light delivered to the tissue site by processor connector 141 and/or processor connector 142. Processor 140 may be configured to perform one or more mathematical operations on the signals received. Processor 140 may further be configured to deliver to display 145 a signal corresponding to mathematical operation(s) performed, data used in performing mathematical operation(s), and/or results of the mathematical operation(s). Display 145 may also receive from any system component signals corresponding to the amount and/or wavelength of light (a) emitted by light source 125, (b) delivered to the tissue site by light emission optics 120, (c) received by light detection optics 130, and/or (d) detected by detector 135.

System 110 may also include water probe location sensor 155. Sensor 155 may be configured to detect and/or receive location information. Location information may include the location and/or orientation of at least a portion of system 110, the location and/or orientation of the site of assessment, and/or the location and/or orientation of a reference point. Sensor 155 also may be configured to deliver a signal corresponding to location information to processor 140 via processor connector 143.

Disposable water probe 150 may include aperture 121, disposable fiber optic cable 122, fiber optic cable connector 123 (not expressly shown), aperture 131, disposable fiber optic cable 132, fiber optic cable connector 133 (not expressly shown), disposable water probe housing 151, spacer 152, and/or seal 153 as shown in FIG. 5B. Spacer 152 may be a separate component of probe 150. Alternatively, it may be formed simply by extending the walls of probe housing 151 a desirable distance beyond light emission aperture and/or light detection aperture. Water probe manipulator 160 may include water probe manipulator housing 161, at least a portion of fiber optic cable 124, and at least a portion of fiber optic cable 134. Water probe manipulator 160 may further include water probe location sensor 155 as shown in FIG. 5B.

Power inlet or power source 117 may deliver power to controller 116 as shown in FIG. 5B. In addition, power inlet or power source 117 may deliver power to keyboard 112, light source 125, light detector 135, processor 140, display 145, and/or location sensor 155. Power inlet or power source 117 may include a transformer and/or a battery (not expressly shown).

In some specific example embodiments, a probe or any portion thereof may be configured to be disposable, repairable, and/or replaceable. For example, an entire probe and/or a probe housing may be sanitized, sterilized, reconditioned, repaired, or replaced between (a) each assessment of a site, (b) each assessment of a subject, and/or (c) each subject (collectively, "each use"). A probe and/or a probe housing may be configured to have at least one sanitized or sterile surface to be placed at or near an assessment site. A sanitized or sterile surface may include a covering, e.g., a disposable disc and/or a disposable sleeve, that may be replaced between each use.

Artisans of ordinary skill will recognize that the exact configuration of systems and devices of the invention may be varied without making them unsuitable for body fluid metric assessment. For example, although the non-limiting specific example embodiments shown in FIGS. 4A-5C shown depict a fiber optic cable between a light detection aperture and a light detector, this fiber optic cable is not essential in all specific example embodiments. In some specific example embodiments, for example, a light detector may be near or in contact with a light detection aperture. Similarly, light emission optics may be configured to deliver up to the entire amount of radiation emitted by a light source to a tissue site without fiber optic cables, e.g., by using direct illumination or one or more mirrors. In addition, while the specific example embodiments shown in FIGS. 4A-5C have only one each of a light emission fiber optic cable, a light emission fiber optic cable connector, a light emission disposable fiber optic cable, a light emission aperture, a light detection aperture, a disposable light detection fiber optic cable, a light detection fiber optic cable connector, and a light detection fiber optic cable, according to other specific example embodiments, a plurality of each may be used. For example, two or more light detection fiber optic cables may be used to enhance the sensitivity of light detection.

According to some specific example embodiments, light emission optics may be tuned to emit radiation at a plurality of narrow spectral wavelengths. For example, a plurality of narrow spectral wavelengths may be chosen so that a biological compound of interest will absorb. A plurality of narrow spectral wavelengths may also be chosen so that the light absorbed by species other than the biological compound of interest is minimized. Reduced absorption by interfering species may be anywhere within a range from just detectably less absorption than the biological compound of interest to zero absorption. For example, the light absorbed by the interfering species may absorb 10% or less than that absorbed by the biological compound of interest.

In other examples, a plurality of narrow spectral wavelengths may be chosen to be preferentially absorbed by tissue water, non-heme proteins, and lipids, where preferentially absorbed wavelengths may be wavelengths whose absorption is substantially independent of the individual concentrations of non-heme proteins and lipids, and is substantially dependent on the sum of the individual concentrations of non-heme proteins and lipids. In further specific example embodiments, a plurality of narrow spectral wavelengths may be chosen to ensure that measured received radiation is substantially insensitive to scattering variations and such that the optical path lengths through the tissue, e.g., dermis, at said wavelengths are substantially equal. In still other specific example embodiments, a plurality of narrow spectral wavelengths may be chosen to ensure that measured received radiation from a tissue location is insensitive to temperature variations, where said wavelengths are temperature isosbestic in the water absorption spectrum or the received radiation is combined in a way that substantially cancels temperature dependencies of the individual wavelengths of received radiation when computing tissue water fractions.

Light emission optics and/or light detection optics may be mounted within the probe housing and positioned with appropriate alignment to enable detection in a transmissive mode and/or a reflective mode. Light emission optics and/or light detection optics may be placed in a remote unit operably connected to a probe housing through optical fibers. Light emission optics may include any electromagnetic radiation emitter. An electromagnetic radiation emitter may include an incandescent light source, a white light source, a light emitting diode ("LED"), and/or a laser (e.g., a Vertical Cavity Surface Emitting Laser). In some specific example embodiments, a laser may be selected for use with a fiber optic sensor according to the high efficiency with which lasers may be coupled into fiber optics.

In some specific example embodiments, a processing device may receive and compare at least two sets of optical measurements, where the at least first set of optical measurements corresponds to the detection of light whose absorption is primarily due to water, lipids and non-heme proteins, and where the at least second set of optical measurements corresponds to the detection of light whose absorption is primary due to water, and where a comparison of said at least two optical measurements provides a measure of the absolute water fraction within said tissue location. In other specific example embodiments, a processing device may receive and compare at least two sets of optical measurements, where said at least two sets of optical measurements are based on received radiation from at least two wavelengths and which are combined to form either a single ratio of said received radiation, a sum of ratios of said received radiation or ratio of ratios of said received radiation. In additional specific example embodiments, a processing device may receive and compare at least two sets of optical measurements from at least two different wavelengths, where absorption of light at said at least two different wavelengths is primarily due to water which is in the vascular blood and in the extravascular tissue, and where a ratio of said at least two measurements provides a measure of a difference between the fractions of water in the blood and surrounding tissue location.

A systems and/or device according to the disclosure may be calibrated with every use, periodically, occasionally, as needed, or as otherwise desired. In some embodiments, a water fluid metric assessment of the disclosure may be effected very little, if at all, by wavelength independent changes in overall light intensity. In some embodiments, however, wavelength dependent changes in light intensity (e.g., "color shifts") may have the potential to effect measurement accuracy. The intensity of a source may be calibrated using, in some embodiments, a Teflon block due to its stable diffuse reflectance. The frequency of calibrations may depend, in part, on the stability of the source.

TABLE 2

|  | FIG. | |
| --- | --- | --- |
|  | 4A, 4B | 5A, 5B, 5C |
| system | 10 | 110 |
| base unit |  | 111 |
| keyboard |  | 112 |
| housing | 15 | 115 |
| trigger | 16 |  |
| controller |  | 116 |
| battery | 17 |  |
| power inlet or source |  | 117 |
| optical fiber bundle |  | 118 |
| optical fiber bundle housing |  | 119 |
| light emission optics | 20 | 120 |
| light emission aperture | 21 | 121 |
| disposable fiber optic cable | 22 | 122 |
| fiber optic cable connector | 23 | 123 |
| fiber optic cable | 24 | 124 |
| light source | 25 | 125 |
| light detection optics | 30 | 130 |
| light detection aperture | 31 | 131 |
| disposable fiber optic cable | 32 | 132 |
| fiber optic cable connector | 33 | 133 |
| fiber optic cable | 34 | 134 |
| light detector | 35 | 135 |
| processor | 40 | 140 |
| processor connector |  | 141 |
| processor connector |  | 142 |
| processor connector |  | 143 |
| display | 45 | 145 |
| water probe | 50 | 150 |
| water probe housing | 51 | 151 |
| spacer | 52 | 152 |
| seal | 53 | 153 |
| water probe connector | 54 | 154 |
| connector tab |  | 154a |
| connector groove |  | 154b |
| water probe location sensor | 55 | 155 |
| location sensor connector |  | 156 |
| probe manipulator |  | 160 |
| probe manipulator housing |  | 161 |

As will be understood by those skilled in the art, other equivalent or alternative methods for the measurement of the water fraction within tissue ($f_w$), as well as shifts in fluid between the intravascular and extravascular compartments, IVF-EVF or Q, according to embodiments of the present disclosure can be envisioned without departing from the essential characteristics thereof. For example, devices of the disclosure may be manufactured in either a handheld or a tabletop configuration, and may be operated sporadically, intermittently, and/or continuously. Moreover, individuals skilled in the art of near-infrared spectroscopy would recognize that additional terms can be added to the algorithms used herein to incorporate reflectance measurements made at additional wavelengths and thus improve accuracy further. Also, light sources or light emission optics other than LED's including and not limited to incandescent light and narrow-band light sources appropriately tuned to the desired wavelengths and associated light detection optics may be placed within the probe housing which may be placed near the tissue location or may be positioned within a remote unit; and which deliver light to and receive light from the probe location via optical fibers. Additionally, optical detectors may function in a forward-scattering mode, a back-scattering mode, a reflection mode, and/or a transmission mode. While the description provides a number of formulas and mathematical operations for calculating body-fluid metrics, it will be appreciated by those of ordinary skill in the art that the same figures may be obtained using comparable alternative formulas and operations. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Example 1

A porcine animal model of over-hydration was used to evaluate the correlation of local and whole-body fat-free percent water. Animals each received one liter of Ringer's lactate solution over 20 minutes of each hour for five hours.

Figure 6:
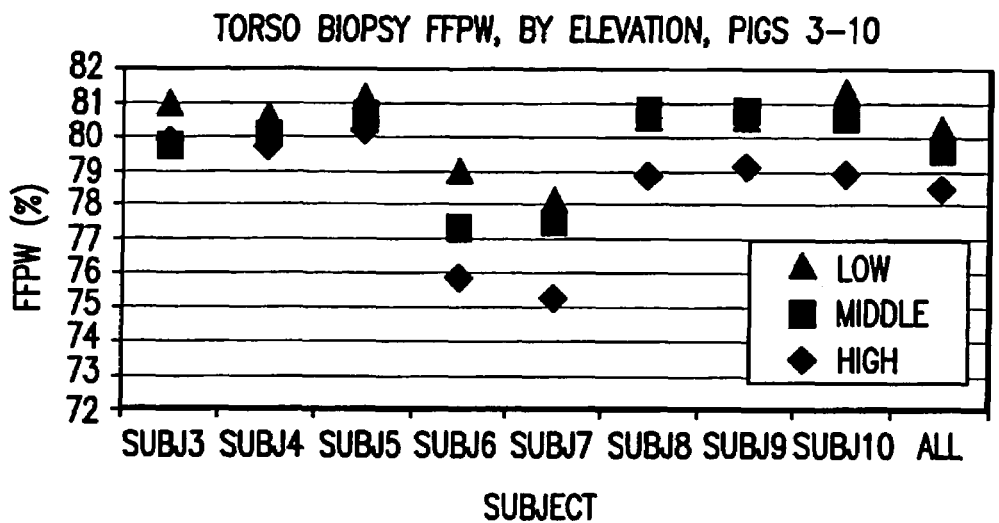
FIG. 6 shows the results of measuring lean water fraction ($f_w^l$) in tissue biopsies taken at different elevations.

Local hydration of animal tissue was assessed in hundreds of torso skin biopsies. Animals were positioned on their sides and three biopsies were taken from each animal, one each from at, above, and below the midline of the torso. The results of this study are shown in FIG. 6. For each animal, $f_w^l$ was significantly higher at low elevation than at high elevation. In addition, $f_w^l$ of the mid-line biopsies strongly correlated with whole-body $f_w^l$.

Without being limited to any particular mechanism of action, these elevation-dependent results may be attributable to movement of extracellular water due to differences in hydrostatic pressure of perhaps 10 cm $H_2O$ (7.5 mm Hg). A very large number of tissue biopsy analyses had to be averaged to demonstrate this relationship, due to the errors inherent in excising bleeding pieces of tissue, followed by the errors inherent in desiccating, defatting, and repeatedly weighing these tiny samples. Similar increases in local tissue hydration have also been observed in human volunteers with sensors on their foreheads when the head was placed below the heart.

Example 2

Figure 7:
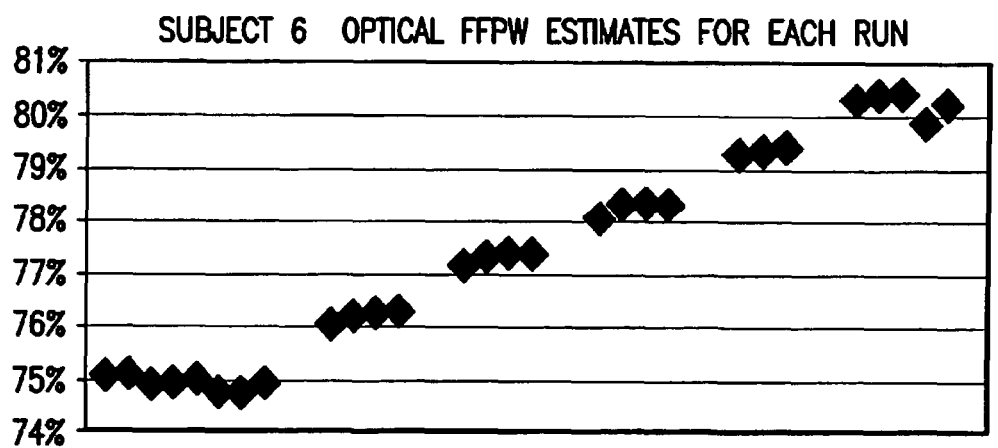
FIG. 7 shows the optical $f_w^l$ estimates with data gathered simultaneously with the tissue biopsies.
Figure 8:
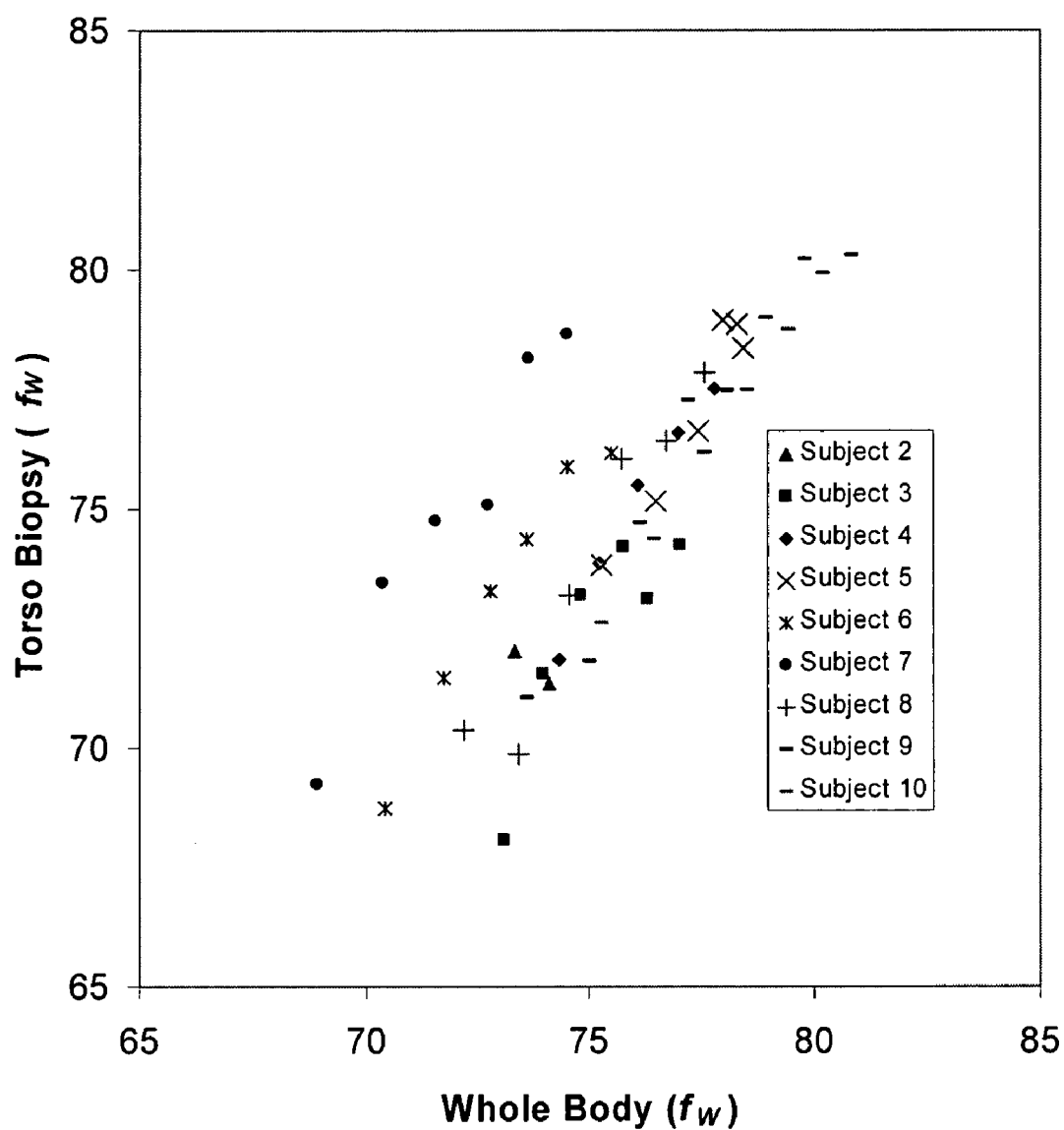
FIG. 8 shows relationship between local and total body water fraction when fat is included ($f_w$). The measurements were made in piglets (age: 1-3 months, body weight: 10-20 kg) that were being administered fluids (1L Lactated Ringer's Solution) intravenously in a series of 1 hour steps. Each fluid bolus was administered over a 20 minute period followed by 40 minutes of equilibration before estimating the local and whole body water fractions. Whole body water as a fraction of whole body mass ($f_w$) was determined by chemical analysis of the homogenized carcass at the end of the experiment. By combining the weight of the animal during the experiment with the post-mortem body composition analysis, and assuming that changes in weight were solely due to changes in water content, the $f_w$ could be determined at any point in the experiment. Tissue biopsies (5-8 mm in diameter and approximately 3 mm deep) were collected from sites across the belly and chest. For each data point displayed in the figures, the results of 3-9 biopsies were averaged, with careful effort to balance the number of biopsies taken from above the center of mass with the number of biopsies taken from below the center of mass. The same chemical analysis methods were used to perform the composition analysis of the whole carcass and local biopsy samples.
Figure 9:
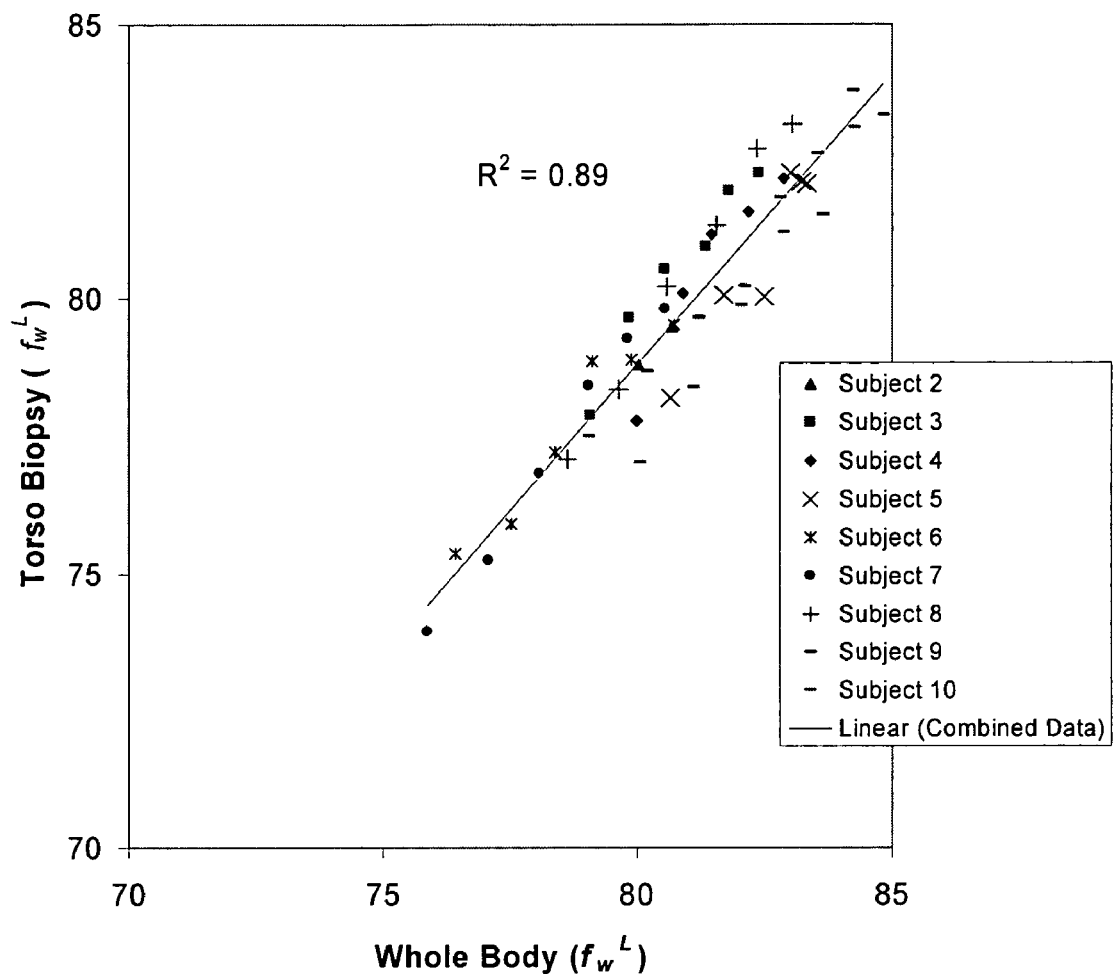
FIG. 9 shows data from the same experiments as FIG. 8, except with the local and total water computed as a fraction of lean mass ($f_w^l$) rather than total mass ($f_w$).

At the same time the tissue biopsies of Example 1 were taken, fat-free percent water was assessed optically. Each sensor was affixed to a single tissue site. Results obtained from consecutive optical $f_w^l$ assessments had a standard deviation of only 0.17%. These results are graphically depicted for a single, typical subject in FIG. 7.

Based on analysis of run-to-run changes in optical $f_w^I$ estimates, a set of two probes affixed to two similar tissue sites having different hydrostatic pressures should be able to resolve differences in local $f_w^I$ with a standard deviation of about 0.25%, and with relatively short measurements, enabling FwEC to be detected with very high precision.

What is claimed is:

1. A method for assessing an extracellular water metric in a subject, said method comprising:
   using at least one sensor:
      emitting light of at least one wavelength toward a tissue site of interest, wherein a portion of the emitted light is reflected by the tissue site of interest;
      detecting at least one wavelength of the light reflected by the tissue site of interest from a position about one millimeter to about five millimeters from the tissue site of interest;
      emitting light of at least one wavelength toward a reference tissue site, wherein a portion of the emitted light is reflected by the reference tissue site;
      detecting at least one wavelength of the light reflected by the reference tissue site from a position about one millimeter to about five millimeters from the reference tissue site; and
   using a processor:
      processing detected reflected light from the tissue site of interest and detected reflected light from the reference tissue site to compute the extracellular water metric, wherein the hydrostatic pressure of the tissue site of interest differs from the hydrostatic pressure of the reference tissue site.

2. A method according to claim 1, wherein the extracellular water metric comprises intravascular water fraction, $f_w^{IV}$, interstitial water fraction $f_w^{IS}$, extracellular water fraction, $f_w^{EC}$, or water balance index, Q or combinations thereof.

3. A method according to claim 1, wherein the extracellular water metric comprises changes in the intravascular water fraction, $\Delta f_w^{IV}$, changes in the interstitial water fraction, $\Delta f_W^{IS}$, changes in the extracellular water fraction, $\Delta f_W^{EC}$, or changes in the water balance index, $\Delta Q$ or combinations thereof.

4. A method according to claim 1, wherein the extracellular water metric is a metric of at least a portion of the subject's whole body.

5. A method according to claim 4 further comprising comparing the extracellular water metric with a control and determining from that comparison whether the at least a portion of the subject's whole body is dehydrated or over-hydrated.

6. A method according to claim 5 further comprising administering a hydration therapy to a dehydrated subject.

7. A method according to claim 5 further comprising administering a dehydration therapy to an over-hydrated subject.

8. A method according to claim 1 further comprising exhibiting the extracellular water metric on a display.

9. A method according to claim 1, wherein detecting at least one wavelength of the light reflected by the tissue site of interest comprises detecting light comprising a wavelength of 950-1400 nm, 1500-1800 nm, or 2000-2300 nm or any combination thereof.

10. A method according to claim 9 wherein the light comprises a wavelength of 1180 nm, 1125 nm, 1168 nm, 1170 nm, 1185 nm, 1190 nm, 1230 nm, 1245 nm, 1250 nm, 1274 nm, 1275 nm, 1300 nm, 1330 nm, 1710 nm, 1730 nm, or 1740 nm, or any combination thereof.

11. A method according to claim 9, wherein detecting at least one wavelength of the light reflected by the tissue site of interest comprises detecting at least two wavelengths of light with a first detector.

12. A method according to claim 11, wherein the wavelengths differ by at least 10 nm.

13. A method according to claim 9, wherein detecting at least one wavelength of the light reflected by the reference tissue site comprises detecting light comprising at least one wavelength within a wavelength band of 950-1400 nm, 1500-1800 nm, or 2000-2300 nm or any combination thereof.

14. A method according to claim 13, wherein the comprises a wavelength of 1180 nm, 1125 nm, 1168 nm, 1170 nm, 1185 nm, 1190 nm, 1230 nm, 1245 nm, 1250 nm, 1274 nm, 1275 nm, 1300 nm, 1330 nm, 1710 nm, 1730 nm, or 1740 nm, or combinations thereof.

15. A method according to claim 13, wherein detecting at least one wavelength of the light reflected by the reference tissue site comprises detecting at least two wavelengths of light with a second detector.

16. A method according to claim 15, wherein the wavelengths differ by at least 10 nm.

17. A method according to claim 1, wherein the emitting light of at least one wavelength toward the tissue site of interest comprises emitting light from a light source and wherein the emitting light of at least one wavelength toward the reference tissue site comprises emitting light from said light source.

18. A method according to claim 1, wherein the emitting light of at least one wavelength toward the tissue site of interest comprises emitting light from a first light source and wherein the emitting light of at least one wavelength toward the reference tissue site comprises emitting light from a second light source.

19. A method according to claim 1, wherein the detecting light of at least one wavelength reflected by the tissue site of interest comprises detecting light with a first detector and wherein the detecting light of at least one wavelength reflected by the reference tissue site comprises detecting light with a second detector.

20. A method according to claim 1, wherein the tissue site of interest and reference tissue site are located at two different sites within a single, contiguous organ.

21. A method according to claim 1, wherein the assessment is substantially independent of light scattering variations and temperature variations.

22. A method according to claim 1, wherein emitting light of at least one wavelength toward a tissue site of interest comprises emitting light with a light source about one millimeter to about five millimeters from the tissue site of interest.

23. A method according to claim 1, wherein emitting light of at least one wavelength toward a tissue site of interest comprises emitting light with a light source about one millimeter to about five millimeters from the reference tissue site.

24. A method according to claim 1, wherein the subject is a mammal.

25. A method according to claim 24, wherein the mammal is a human.

26. A method, for assessing an extracellular water metric in a subject, the method comprising:
   using at least one sensor:
      emitting light of at least one wavelength toward a tissue site of interest, wherein a portion of the emitted light is reflected by the tissue site of interest;

detecting at least one wavelength of the light reflected by the tissue site of interest from a position about one millimeter to about five millimeters from the tissue site of interest;

emitting light of at least one wavelength toward a reference tissue site, wherein a portion of the emitted light is reflected by the reference tissue site;

detecting at least one wavelength of the light reflected by the reference tissue site from a position about one millimeter to about five millimeters from the reference tissue site; and using a processor:

processing detected reflected light from the tissue site of interest and detected reflected light from the reference tissue site to compute the extracellular water metric, wherein the detecting light of at least one wavelength reflected by the tissue site of interest comprises detecting light with a detector and wherein the detecting light of at least one wavelength reflected by the reference tissue site comprises detecting light with said detector.

27. A method, for assessing an extracellular water metric in a subject, the method comprising:

using at least one sensor:

emitting light of at least one wavelength toward a tissue site of interest, wherein a portion of the emitted light is reflected by the tissue site of interest;

detecting at least one wavelength of the light reflected by the tissue site of interest from a position about one millimeter to about five millimeters from the tissue site of interest;

emitting light of at least one wavelength toward a reference tissue site, wherein a portion of the emitted light is reflected by the reference tissue site;

detecting at least one wavelength of the light reflected by the reference tissue site from a position about one millimeter to about five millimeters from the reference tissue site; and using a processor:

processing detected reflected light from the tissue site of interest and detected reflected light from the reference tissue site to compute the extracellular water metric, wherein the tissue site of interest and reference tissue site are located within different organs.

28. A method, for assessing an extracellular water metric in a subject, the method comprising:

using at least one sensor:

emitting light of at least one wavelength toward a tissue site of interest, wherein a portion of the emitted light is reflected by the tissue site of interest;

detecting at least one wavelength of the light reflected by the tissue site of interest from a position about one millimeter to about five millimeters from the tissue site of interest;

emitting light of at least one wavelength toward a reference tissue site, wherein a portion of the emitted light is reflected by the reference tissue site;

detecting at least one wavelength of the light reflected by the reference tissue site from a position about one millimeter to about five millimeters from the reference tissue site; and using a processor:

processing detected reflected light from the tissue site of interest and detected reflected light from the reference tissue site to compute the extracellular water metric, wherein the tissue site of interest and reference tissue site are at substantially the same site under differing hydrostatic pressures, wherein the hydrostatic pressure of the tissue site of interest is altered to differ from the hydrostatic pressure of the reference tissue site.

29. A method, for assessing an extracellular water metric in a subject, the method comprising:

using at least one sensor:

emitting light of at least one wavelength toward a tissue site of interest, wherein a portion of the emitted light is reflected by the tissue site of interest;

detecting at least one wavelength of the light reflected by the tissue site of interest from a position about one millimeter to about five millimeters from the tissue site of interest;

emitting light of at least one wavelength toward a reference tissue site, wherein a portion of the emitted light is reflected by the reference tissue site;

detecting at least one wavelength of the light reflected by the reference tissue site from a position about one millimeter to about five millimeters from the reference tissue site; and using a processor:

processing detected reflected light from the tissue site of interest and detected reflected light from the reference tissue site to compute the extracellular water metric;

and further comprising:

(a) excising from the subject the site of interest before the emitting;

(b) excising from the subject the reference site before the emitting, or (c) excising from the subject both the site of interest and the reference site before the emitting.

30. A system for assessing an extracellular fluid metric in a subject, said system comprising:

a local fluid content probe configured to assess a local fluid content metric at a tissue site;

a location information sensor configured to assess location information of the probe, the tissue site of interest, or the probe and the tissue site of interest; and a processor, wherein the processor is operably coupled to the local fluid content probe, operably coupled to the location information sensor, and configured to process a local fluid content metric and location information to produce an extracellular fluid metric.

* * * * *

UNITED STATES PATENT AND TRADEMARK OFFICE
CERTIFICATE OF CORRECTION

PATENT NO. : 7,657,292 B2
APPLICATION NO. : 11/283506
DATED : February 2, 2010
INVENTOR(S) : Baker, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1111 days.

Signed and Sealed this

Thirtieth Day of November, 2010

David J. Kappos
*Director of the United States Patent and Trademark Office*